United States Patent
Kose

(10) Patent No.: US 11,839,976 B2
(45) Date of Patent: Dec. 12, 2023

(54) CONTROL SYSTEM FOR CONTINUUM ROBOT, CONTROL METHOD FOR CONTINUUM ROBOT, AND STORAGE MEDIUM

(71) Applicant: CANON KABUSHIKI KAISHA, Tokyo (JP)

(72) Inventor: Hidekazu Kose, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 363 days.

(21) Appl. No.: 17/378,284

(22) Filed: Jul. 16, 2021

(65) Prior Publication Data

US 2022/0032456 A1 Feb. 3, 2022

(30) Foreign Application Priority Data

Jul. 29, 2020 (JP) .................................. 2020-128130

(51) Int. Cl.
| | |
|---|---|
| B25J 9/16 | (2006.01) |
| B25J 9/06 | (2006.01) |
| B25J 9/10 | (2006.01) |

(52) U.S. Cl.
CPC ............. B25J 9/1625 (2013.01); B25J 9/065 (2013.01); B25J 9/1045 (2013.01); G05B 2219/40234 (2013.01); G05B 2219/41413 (2013.01)

(58) Field of Classification Search
CPC ........ B25J 9/1625; B25J 9/065; B25J 9/1045; B25J 9/104; B25J 9/00; B25J 9/0009; B25J 9/16; G05B 2219/40234; G05B 2219/41413; A61B 2034/2051; A61B 2034/301; A61B 2090/061; A61B 2090/067; A61B 34/71
USPC .... 318/319, 568.12, 568.11, 568.1, 567, 560
See application file for complete search history.

(56) References Cited

U.S. PATENT DOCUMENTS 7,477,965 B2 * 1/2009 Soham ................ F16H 19/0654
72/299
2018/0140168 A1 5/2018 Haraguchi

FOREIGN PATENT DOCUMENTS

| CN | 1250516 A | 4/2000 |
|---|---|---|
| CN | 1258826 A | 7/2000 |
| EP | 1267701 B1 | 10/2007 |
| JP | 2010104426 A | 5/2010 |
| JP | 5259340 B2 | 8/2013 |
| JP | 2019122491 A | 7/2019 |

* cited by examiner

*Primary Examiner* — David Luo
(74) *Attorney, Agent, or Firm* — Canon U.S.A., Inc. IP Division

(57) ABSTRACT

A control system for a continuum robot includes a kinematics calculation unit configured to calculate a length of a wire in a bendable portion. The kinematics calculation unit includes a wire length calculation unit configured to calculate, for each of a plurality of minute sections obtained by dividing the bendable portion in a longitudinal direction thereof, a length of the wire in the minute section based on a bending angle, a turning angle, and a torsional angle of the minute section, and an addition unit configured to add the lengths of the wire in the plurality of minute sections obtained by the wire length calculation unit to calculate the length of the wire in the bendable portion.

7 Claims, 13 Drawing Sheets

CONTROL SYSTEM FOR CONTINUUM ROBOT, CONTROL METHOD FOR CONTINUUM ROBOT, AND STORAGE MEDIUM

BACKGROUND

Field of the Disclosure

The present disclosure relates to a control system for a continuum robot including a bendable portion configured to be bent by driving of a wire, a control method for the continuum robot, and a storage medium storing a program for causing a computer to function as the control system.

Description of the Related Art

In recent years, a minimally invasive medical treatment for reducing a burden on a patient and improving the quality of life (QOL) after treatment or examination has been attracting attention. Typical examples of the minimally invasive medical treatment include surgery or examination using an endoscope. For example, laparoscopic surgery enables a surgical wound to be made smaller than in the case of conventional laparotomy surgery, and is thus advantageous not only in that the hospitalization period required after surgery can be shortened, but also in that the laparoscopic surgery is cosmetically superior.

A flexible endoscope is known as an example of the endoscope used for the minimally invasive medical treatment. Such a flexible endoscope includes an insertion portion functioning as a bendable portion formed of a bendable member. The flexible endoscope can thus reach a deep portion of the body without pressuring the tissue of a tortuous organ, such as an esophagus, a large intestine, or a lung, which makes it possible to reduce the burden on the patient. In addition, it can be expected that the burden on the patient can be further reduced, for example, by using a drive unit such as an actuator to drive the bendable portion serving as the insertion portion, and automatically controlling the attitude of the bendable portion along a path in the body. Accordingly, the search and development of a mechanism and a control method for a continuum robot that can be used as the flexible endoscope have been actively conducted.

Many of such continuum robots adopt a method in which a drive unit such as an actuator for driving a wire is installed in a base, and the wire is used as a driving force transmission mechanism for bending the bendable portion, thereby decreasing the diameter of the bendable portion. This method enables a continuum robot to reach a deep portion of the body. However, the rigidity of the bendable portion of the continuum robot decreases as the diameter of the bendable portion is decreased. Accordingly, if the bendable portion of the continuum robot comes into contact with an inner wall of a body cavity or the like, the continuum robot (bendable portion) may be twisted about a central axis of the continuum robot. Due to the occurrence of the twist, the correspondence between the amount of driving of the wire and the attitude of the continuum robot (bendable portion) deviates from a designed value, which may lead to deterioration in the accuracy of the control performance of the continuum robot (bendable portion). In this regard, for example, Japanese Patent Application Laid-Open No. 2019-122491 discusses a technique in which, even when the bendable portion of the continuum robot is twisted, the driving displacement amount of the wire is controlled based on the torsional amount of the bendable portion, so that the attitude of the bendable portion is matched with a target attitude.

According to the technique discussed in Japanese Patent Application Laid-Open No. 2019-122491, in order to compensate for a control error due to the twist of the bendable portion, the length of the wire that passes through the bendable portion is calculated assuming that a value of the phase angle of the wire that passes through the position (proximal end) of the bendable portion closest to the base, which is obtained considering the torsional amount, is a new phase angle. In the technique discussed in Japanese Patent Application Laid-Open No. 2019-122491, it is assumed that the wire moves linearly from the proximal end of the bendable portion to a wire guide located at the position (distal end) of the bendable portion farthest from the base. However, in the actual continuum robot, if the bendable portion is twisted, the wire moves in a spiral along the central axis of the continuum robot (bendable portion). Thus, in the technique discussed in Japanese Patent Application Laid-Open No. 2019-122491, the length of the wire in the bendable portion (the length of the wire that passes through the bendable portion) cannot be accurately calculated when the bendable portion of the continuum robot is twisted. As a result, it is difficult to improve the control performance of the continuum robot.

SUMMARY

The present disclosure is directed to providing a mechanism that can achieve an improvement in the control performance of a continuum robot even when a bendable portion of the continuum robot is twisted.

According to an aspect of the present disclosure, a control system for a continuum robot including a bendable portion configured to be bent by driving of a wire, and a drive unit configured to drive the wire includes a torsional angle acquisition unit configured to acquire a torsional angle of the bendable portion, and a kinematics calculation unit configured to calculate a length of the wire in the bendable portion based on the torsional angle acquired by the torsional angle acquisition unit. The kinematics calculation unit includes a wire length calculation unit configured to calculate, for each of a plurality of minute sections obtained by dividing the bendable portion in a longitudinal direction thereof, a length of the wire in the minute section based on a bending angle, a turning angle, and a torsional angle of the minute section, and an addition unit configured to add the lengths of the wire in the plurality of minute sections obtained by the wire length calculation unit to calculate the length of the wire in the bendable portion.

The present disclosure also includes a control method for the continuum robot using the above-described control system, and a storage medium storing a program for causing a computer to function as the above-described control system.

According to exemplary embodiments of the present disclosure, the length of a wire in a bendable portion of a continuum robot can be accurately calculated even when the bendable portion is twisted, which leads to an improvement in the control performance of the continuum robot.

Further features of the present disclosure will become apparent from the following description of exemplary embodiments with reference to the attached drawings.

DESCRIPTION OF THE EMBODIMENTS

Various exemplary embodiments, features, and aspects of the present disclosure will be described below with reference to the drawings. The exemplary embodiments described below illustrate examples assuming that a continuum robot uses a wire as a driving force transmission mechanism for bending a bendable portion. Furthermore, a control system and a control method according to an exemplary embodiment of the present disclosure are applied to the continuum robot. In the exemplary embodiments described below, the length of a wire in the bendable portion is calculated assuming that the wire moves in a spiral along a central axis of the continuum robot (the bendable portion), thereby improving the control performance of the continuum robot.

A first exemplary embodiment of the present disclosure will be described.

<1-1. Modeling>

Figure 1:
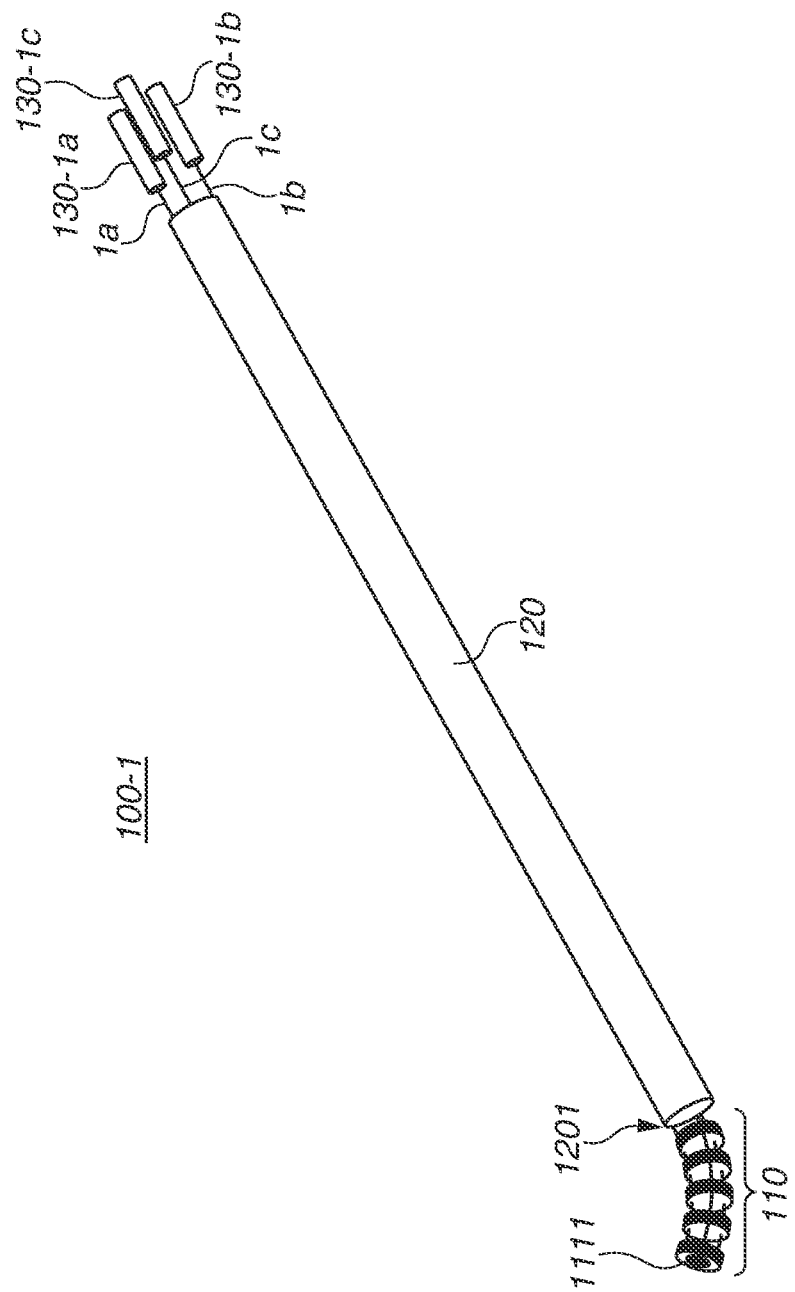
FIG. 1 is a diagram illustrating an example of an external configuration of a continuum robot used in a first exemplary embodiment of the present disclosure.

FIG. 1 illustrates an example of an external configuration of a continuum robot 100 used in the present exemplary embodiment. The continuum robot 100 according to the present exemplary embodiment is hereinafter referred to as a "continuum robot 100-1". The continuum robot 100-1 illustrated in FIG. 1 includes a bendable portion 110 including a wire 1a, a wire 1b, and a wire 1c, a long portion 120, and actuators 130-1a to 130-1c (hereinafter also collectively referred to as actuators 130).

The bendable portion 110 is a component configured to be bent three-dimensionally by driving of at least one of the wires 1a to 1c. In the present exemplary embodiment, a configuration in which the continuum robot 100-1 includes a single bendable portion (the bendable portion 110) configured to be bent three-dimensionally is assumed and described. A distal end 111 (see FIG. 2) of the bendable portion 110 is provided with a small sensor coil 1111 for detecting a torsional angle $\tau_1$ indicating a torsional amount about a central axis 113 (see FIG. 3) of the bendable portion 110.

The long portion 120 is a component that includes the wires 1a to 1c and is configured to be bent passively by, for example, an external force. In the example illustrated in FIG. 1, it is assumed that the bendable portion 110 ranges from a proximal end corresponding to a front end face 1201 of the long portion 120 to the distal end 111 at which the sensor coil 1111 is provided.

The actuators 130-1a to 130-1c are drive units that drive the wires 1a to 1c. More specifically, the actuator 130-1a drives the wire 1a, the actuator 130-1b drives the wire 1b, and the actuator 130-1c drives the wire 1c.

Figure 2:
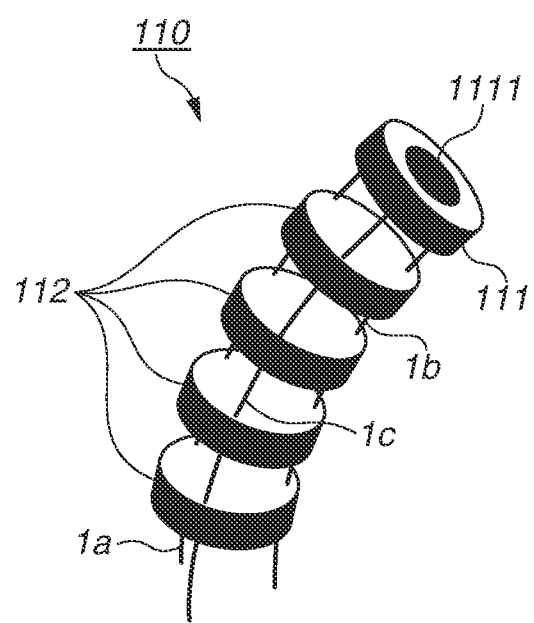
FIG. 2 is an enlarged diagram illustrating a schematic configuration of a bendable portion illustrated in FIG. 1.

FIG. 2 is an enlarged diagram illustrating a schematic configuration of the bendable portion 110 illustrated in FIG. 1. In FIG. 2, components similar to those illustrated in FIG. 1 are denoted by the same reference numerals and the detailed descriptions thereof will be omitted.

The wires 1a to 1c are guided by a plurality of wire guides 112 illustrated in FIG. 2 and a hole formed in the long portion 120 illustrated in FIG. 1. Each of the wires 1a to 1c has one end that is connected to the distal end 111 (the wire guide provided with the sensor coil 1111) of the bendable portion 110 illustrated in FIG. 2, and the other end that is connected to the corresponding one of the actuators 130-1a to 130-1c illustrated in FIG. 1. In the present exemplary embodiment, when the actuators 130-1a to 130-1c are driven in the direction of the central axis 113 of the bendable portion 110, the wires 1a to 1c are each pushed or pulled, thereby enabling the bendable portion 110 to be bent three-dimensionally.

Figure 3:
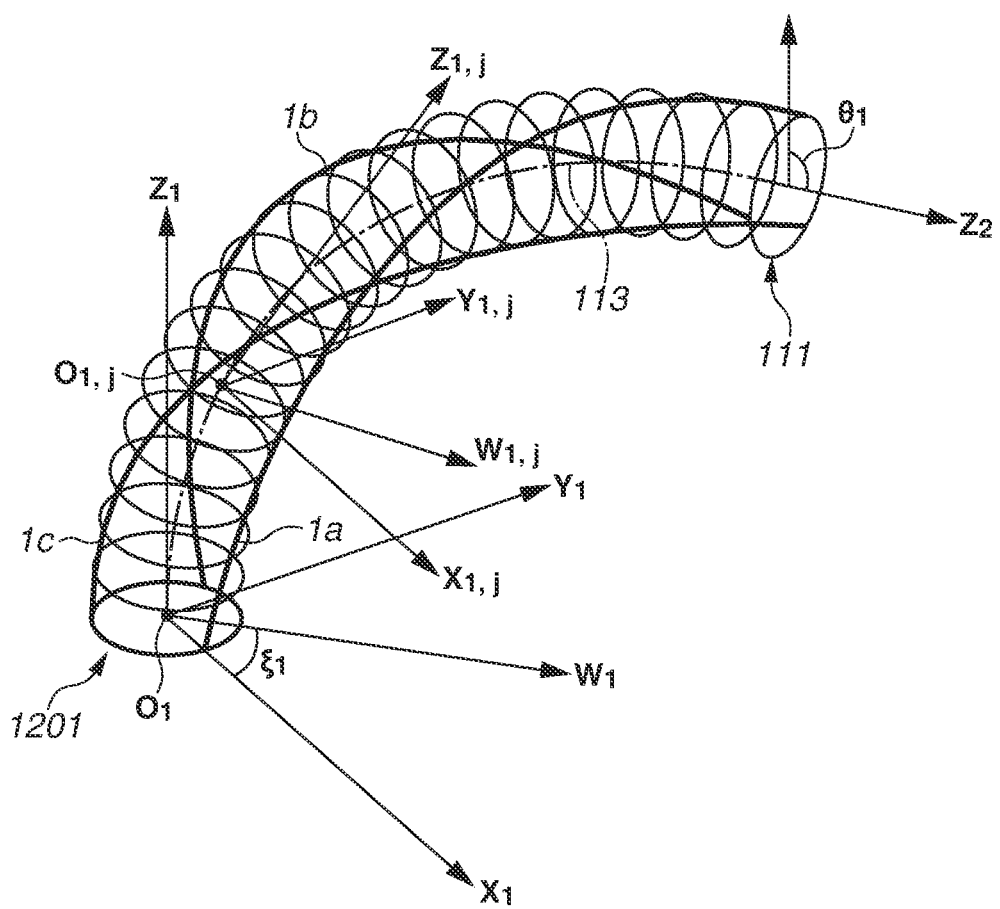
FIG. 3 is a diagram illustrating an example of a model for the bendable portion illustrated in FIG. 1.

FIG. 3 illustrates an example of a model for the bendable portion 110 illustrated in FIG. 1. More specifically, FIG. 3 is a diagram for deriving a model in which the wires 1a to 1c move in a spiral along the central axis 113 of the bendable portion 110 of the continuum robot 100-1. In the present exemplary embodiment, the model illustrated in FIG. 3 is used to consider a twist of the bendable portion 110 of the continuum robot 100-1, and a continuum robot control device 200 (see FIG. 5) that provides a control input for matching the attitude of the bendable portion 110 with a target attitude is designed.

The following is definitions of symbols used in the present exemplary embodiment.

$\theta_1$: Absolute bending angle of the first bendable portion 110
$\zeta_1$: Absolute turning angle of the first bendable portion 110
$\tau_1$: Absolute torsional angle of the first bendable portion 110
$l_{1a1}$: Length of the wire 1a in the first bendable portion 110
$l_{1b1}$: Length of the wire 1b in the first bendable portion 110
$l_{1c1}$: Length of the wire 1c in the first bendable portion 110
$r_g$: Distance from the central axis 113 of the bendable portion 110 to each of the wires 1a to 1c
$l_{10}$: Length of each of the wires 1a to 1c in the first bendable portion 110 having a bending angle of 0 degree
$\Delta\theta_{1,j}$: Bending angle of the j-th minute section of the first bendable portion 110
$\Delta l_{1,j}$: Length of the j-th minute section of the first bendable portion 110

In FIG. 3, each of the wires 1a to 1c in the bendable portion 110 is indicated by a thick solid line, and the central axis 113 of the bendable portion 110 is indicated by a dashed-dotted line. Also in FIG. 3, each cross section obtained by virtually dividing the bendable portion 110 into $m_1$ minute sections in the longitudinal direction of the bendable portion 110, i.e., the direction of the central axis 113 is indicated by a thin solid line (wherein $m_1$ is the number of minute sections).

In the model for the bendable portion 110 illustrated in FIG. 3, the center of the front end face 1201 of the long portion 120 corresponding to the proximal end of the bendable portion 110 illustrated in FIG. 1 is defined as an origin $O_1$. In the model for the bendable portion 110 illustrated in FIG. 3, a $Z_1$-axis is provided in the direction of the central axis 113 in the front end face 1201, an $X_1$-axis is provided in the direction from the origin $O_1$ to the position of the wire 1a in the front end face 1201, and a $Y_1$-axis is provided in the direction orthogonal to each of the $X_1$-axis and the $Z_1$-axis. In addition, in the model for the bendable portion 110 illustrated in FIG. 3, a $Z_2$-axis is provided in the direction of the central axis 113 at the distal end 111 of the bendable portion 110, and an angle formed between the $Z_1$-axis and the $Z_2$-axis is defined as the bending angle $\theta_1$ of the bendable portion 110. Furthermore, in the model for the bendable portion 110 illustrated in FIG. 3, a $W_1$-axis is provided in the direction from the origin $O_1$ to the center of the distal end 111 within an $X_1$-$Y_1$ plane, and an angle formed between the $X_1$-axis and the $W_1$-axis is defined as the turning angle $\zeta_1$ of the bendable portion 110.

When the bendable portion 110 of the continuum robot 100-1 is not twisted, the wires 1a to 1c move on a plane parallel to a $W_1$-$Z_1$ plane. Accordingly, the length of each of the wires 1a to 1c can be easily calculated even when the wires 1a to 1c are treated as a continuum.

On the other hand, when the bendable portion 110 of the continuum robot 100-1 is twisted, as illustrated in FIG. 3, each of the wires 1a to 1c moves in a spiral along the central axis 113 in the longitudinal direction of the bendable portion 110. Accordingly, if the length of each of the wires 1a to 1c is calculated while the wires 1a to 1c are treated as a continuum, complicated calculations become involved, which leads to an increase in the calculation load on the continuum robot control device 200. Therefore, in the present exemplary embodiment, a discretization is performed by virtually dividing the bendable portion 110 into a plurality of minute sections in the longitudinal direction (the direction of the central axis 113) as illustrated in FIG. 3. In each minute section obtained by the division, each of the wires 1a to 1c is approximated to a linear shape to calculate the length of each of the wires 1a to 1c. FIG. 3 illustrates a coordinate system for the j-th (j=1, 2, ..., $m_1$) minute section counted from the front end face 1201. In the coordinate system for the j-th minute section, a $Z_{1,j}$-axis is provided in the direction of the distal end 111 with a center on the front end face 1201 side as an origin $O_{1,j}$, an $X_{1,j}$-axis is provided on a plane that is orthogonal to the $Z_{1,j}$-axis and is flush with the $X_1$-axis, and a $Y_{1,j}$-axis is provided in the direction orthogonal to each of the $X_{1,j}$-axis and the $Z_{1,j}$-axis. Furthermore, a $W_{1,j}$-axis is provided on the line of intersection of an $X_{1,j}$-$Y_{1,j}$ plane and the $W_1$-$Z_1$ plane.

Figure 4:
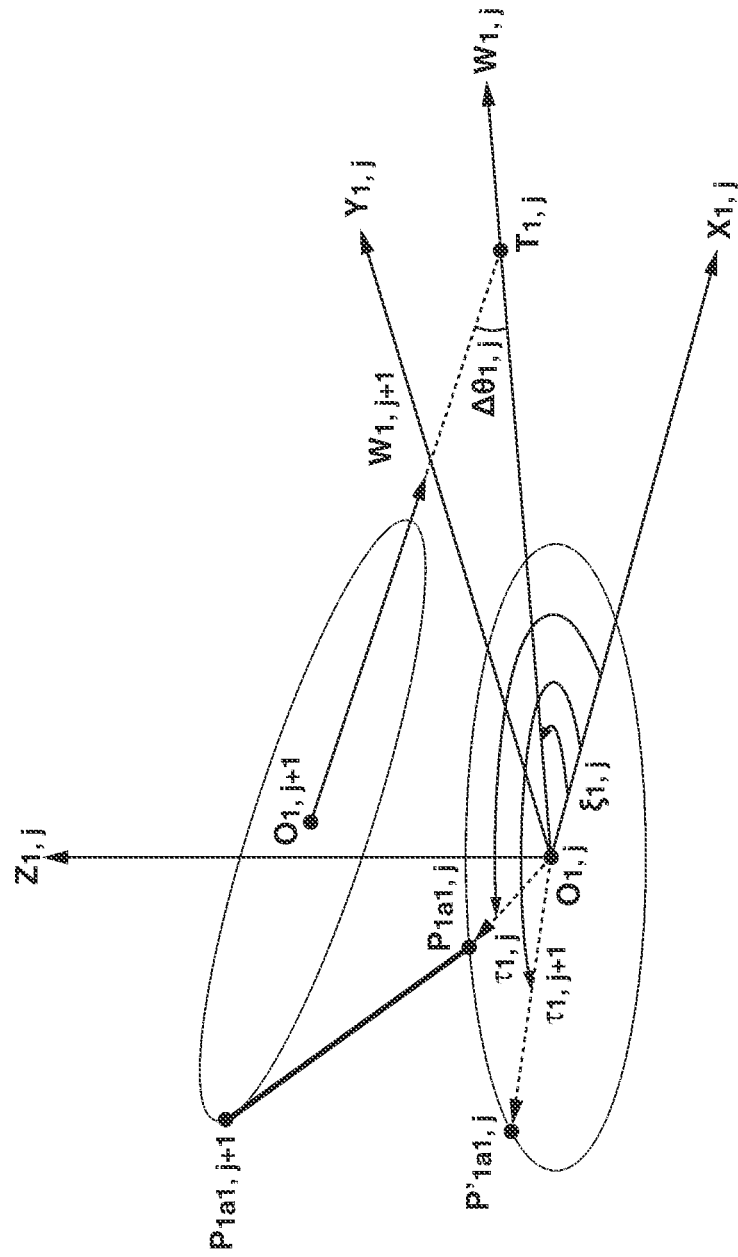
FIG. 4 is a diagram illustrating an example of a model for a j-th minute section illustrated in FIG. 3.

FIG. 4 illustrates an example of a model for the j-th minute section illustrated in the FIG. 3.

As illustrated in FIG. 4, an intersection between the $W_{1,j}$-axis and a $W_{1,j+1}$-axis is defined as a point $T_{1,j}$. In this case, an angle formed between a vector connecting the origin $O_{1,j}$ and the point $T_{1,j}$ and a vector connecting an origin $O_{1,j+1}$ and the point $T_{1,j}$ is defined as the bending angle $\Delta\theta_{1,j}$ of the j-th minute section as illustrated in FIG. 4. In addition, in FIG. 4, an intersection between the wire 1a and a plane closer to the front end face 1201 in the j-th minute section is defined as a point $P_{1a1,j}$, and an angle formed between the $X_{1,j}$-axis and a vector connecting the origin $O_{1,j}$ and the point $P_{1a1,j}$ is defined as a wire torsional angle (also referred to as a "torsional angle") $\tau_{1,j}$. Furthermore, in FIG. 4, an intersection between the wire 1a and a plane closer to the distal end 111 in the j-th minute section is defined as a point $P_{1a1,j+1}$, and a projected point on the $X_{1,j}$-$Y_{1,j}$ plane at the point $P_{1a1,j+1}$ is defined as a point $P'_{1a1,j}$. In this case, an angle formed between the $X_{1,j}$-axis and a vector connecting the origin $O_{1,j}$ and the point $P'_{1a1,j}$ is defined as a torsional angle $\tau_{1,j+1}$ of the (j+1)-th minute section.

In the present exemplary embodiment, the following assumptions are made to derive the model for the bendable portion 110 of the continuum robot 100-1.

Assumption 1: Each of the wires 1a to 1c has a linear shape in each minute section.

Assumption 2: The bendable portion 110 is deformed with a constant curvature.

Assumption 3: The torsional angle continuously changes at a constant rate regardless of a frictional force acting between the wire guides 112 and each of the wires 1a to 1c, and without being influenced by the wire guides 112.

Assumption 4: The expansion and contraction of the wires 1a to 1c is not taken into consideration.

First, a length $l_{1a1,j}$ of the wire 1a that passes through the j-th minute section of the bendable portion 110 is derived. Based on Assumption 1, the length $l_{1a1,j}$ of the wire 1a corresponds to the length of a line segment $P_{1a1,j}$-$P_{1a1,j+1}$ illustrated in FIG. 4. A vector $p_{1a1,j}$ from the origin $O_{1,j}$ to the point $P_{1a1,j}$ is represented by the following expression (1).

$$p_{1a1,j} = [r_g \cos(\tau_{1,j}) \, r_g \sin(\tau_{1,j}) \, 0]^T \qquad (1)$$

A vector $p'_{1a1,j}$ from the origin $O_{1,j}$ to the point $P'_{1a1,j}$ is represented by the following expression (2).

$$p_{1a1,j} = [r_g \cos(\tau_{1,j+1}) \, r_g \sin(\tau_{1,j+1}) \, 0]^T \qquad (2)$$

A vector $t_{1,j}$ from the origin $O_{1,j}$ to the point $T_{1,j}$ is represented by the following expression (3).

$$t_{1,j} = \left[\frac{\Delta l_{1,j}}{\Delta \theta_{t,j}}\cos(\zeta_{1,j}) \, \frac{\Delta l_{1,j}}{\Delta \theta_{t,j}}\sin(\zeta_{1,j}) \, 0\right]^T \qquad (3)$$

If the bendable portion 110 is divided into minute sections each having the same length, the length $\Delta l_{1,j}$ of the j-th minute section is represented by the following expression (4).

$$\Delta l_{1,j} = \frac{l_{10}}{m_1} \qquad (4)$$

In this case, based on Assumption 2 and Assumption 3, the bending angle $\Delta\theta_{1,j}$, a turning angle $\zeta_{1,j}$, and the torsional angle $\tau_{1,j}$ of the j-th minute section are respectively represented by the following expressions (5), (6), and (7) using the bending angle $\theta_1$, the turning angle $\zeta_1$, and the torsional angle $\zeta_1$ of the bendable portion 110.

$$\Delta\theta_{1,j} = \frac{\theta_1}{m_1} \qquad (5)$$

$$\zeta_{1,j} = \zeta_1 \qquad (6)$$

$$\tau_{1,j} = \frac{\tau_1}{m_1}(j-1) \qquad (7)$$

The point $P_{1a1,j+1}$ is a point obtained by rotating the point $P'_{1a1,j}$ about an axis that passes through the point $T_{1,j}$ and is orthogonal to a $W_{1,j}$-$Z_{1,j}$ plane, by the amount corresponding to the bending angle $\Delta\theta_{1,j}$. Accordingly, assuming that a rotation matrix for rotating the point about the $Z_{1,j}$-axis by the amount corresponding to the turning angle $\zeta_{1,j}$ with the origin $O_{1,j+1}$ as a center is represented by $Rz(\zeta_{1,j})$ and a rotation matrix for rotating the point about the $Y_{1,j}$-axis by the amount corresponding to the bending angle $\Delta\theta_{1,j}$ is represented by $Ry(\Delta\theta_{1,j})$, a vector $p_{1a1,j+1}$ from the origin $O_{1,j}$ to the point $P_{1a1,j+1}$ is represented by the following expression (8) using the vector $p'_{1a1,j}$ and the vector $t_{1,j}$.

$$p_{1a1,j+1} = R_z(\zeta_{1,j})R_y(\Delta\theta_{1,j})R_z(p'_{1a1,j}-t_{1,j})+t_{1,j} \qquad (8)$$

In this case, the matrix $Rz(\zeta_{1,j})$ and the matrix $Ry(\Delta\theta_{1,j})$ are obtained by the following expressions (9) and (10), respectively.

$$R_z(\zeta_{1,j}) = \begin{bmatrix} \cos(\zeta_{1,j}) & -\sin(\zeta_{1,j}) & 0 \\ \sin(\zeta_{1,j}) & \cos(\zeta_{1,j}) & 0 \\ 0 & 0 & 1 \end{bmatrix} \qquad (9)$$

$$R_y(\Delta\theta_{1,j}) = \begin{bmatrix} \cos(\Delta\theta_{1,j}) & 0 & \sin(\Delta\theta_{1,j}) \\ 0 & 1 & 0 \\ -\sin(\Delta\theta_{1,j}) & 0 & \cos(\Delta\theta_{1,j}) \end{bmatrix} \qquad (10)$$

As described above, the length $l_{1a1,j}$ of the wire $1a$ that passes through the j-th minute section corresponds to the length of the line segment $P_{1a1,j}$-$P_{1a1,j+1}$. Accordingly, the length $l_{1a1,j}$ of the wire $1a$ is represented by the following expression (11).

$$l_{1a1,j} = |p_{1a1,j+1} - p_{1a1,j}| \qquad (11)$$

Based on Assumption 4, the length $l_{1a1}$ of the wire lain the bendable portion 110 (i.e., the overall length of the wire $1a$ that passes through the bendable portion 110) is the sum of the lengths of the wire $1a$ in the respective minute sections of the bendable portion 110. Accordingly, the length $l_{1a1}$ of the wire $1a$ in the bendable portion 110 is represented by the following expression (12).

$$l_{1a1} = \sum_{j=1}^{m_1} l_{1a1,j} = \sum_{j=1}^{m_1} |p_{1a1,j+1} - p_{1a1,j}| \qquad (12)$$

Next, the wires $1b$ and $1c$ will be described, similarly to the case of the wire $1a$ described above. Assuming that an intersection between the wire $1b$ and a plane closer to the front end face 1201 in the j-th minute section is defined as a point $P_{1b1,j}$ and an intersection between the wire $1c$ and a plane closer to the front end face 1201 in the j-th minute section is defined as a point $P_{1c1,j}$, a vector $p_{1b1,j}$ from the origin $O_{1,j}$ to the point $P_{1b1,j}$ is represented by the following expression (13) and a vector $p_{1c1,j}$ from the origin $O_{1,j}$ to the point $P_{1c1,j}$ is represented by the following expression (14).

$$p_{1b1,j} = \left[ r_g \cos\left(\tau_{1,j} + \frac{2\pi}{3}\right) r_g \sin\left(\tau_{1,j} + \frac{2\pi}{3}\right) 0 \right]^T \qquad (13)$$

$$p_{1c1,j} = \left[ r_g \cos\left(\tau_{1,j} + \frac{4\pi}{3}\right) r_g \sin\left(\tau_{1,j} + \frac{4\pi}{3}\right) 0 \right]^N \qquad (14)$$

A vector $p'_{1b1,j}$ from the origin $O_{1,j}$ to a projected point $P'_{1b1,j}$ and a vector $p'_{1c1,j}$ from the origin $O_{1,j}$ to a projected point $P'_{1c1,j}$ are represented by the following expressions (15) and (16), respectively.

$$p'_{1b1,j} = \left[ r_g \cos\left(\tau_{1,j+1} + \frac{2\pi}{3}\right) r_g \sin\left(\tau_{1,j+1} + \frac{2\pi}{3}\right) 0 \right]^T \qquad (15)$$

$$p'_{1c1,j} = \left[ r_g \cos\left(\tau_{1,j+1} + \frac{4\pi}{3}\right) r_g \sin\left(\tau_{1,j+1} + \frac{4\pi}{3}\right) 0 \right]^T \qquad (16)$$

A vector $p_{1b1,j+1}$ from the origin $O_{1,j}$ to an intersection $P_{1b1,j+1}$ between the wire $1b$ and a plane closer to the distal end 111 in the j-th minute section, and a vector $p_{1c1,j+1}$ from the origin $O_{1,j}$ to an intersection $P_{1c1,j+1}$ between the wire $1c$ and a plane closer to the distal end 111 in the j-th minute section are represented by the following expressions (17) and (18), respectively.

$$p_{1b1,j+1}R_z(\zeta_{1,j})R_y(\Delta\theta_{1,j})R_z(-\zeta_{1,j})(p'_{1b1,j}-t_{1,j})+t_{1,j} \qquad (17)$$

$$p_{1c1,j+1}R_z(\zeta_{1,j})R_y(\Delta\theta_{1,j})R_z(-\zeta_{1,j})(p'_{1c1,j}-t_{1,j})+t_{1,j} \qquad (18)$$

Accordingly, the length $l_{1b1}$ of the wire $1b$ in the bendable portion 110 and the length $l_{1c1}$ of the wire $1c$ in the bendable portion 110 are represented by the following expressions (19) and (20), respectively.

$$l_{1b1} = \sum_{j=1}^{m_1} |p_{1b1,j+1} - p_{1b1,j}| \qquad (19)$$

$$l_{1c1} = \sum_{j=1}^{m_1} |p_{1c1,j+1} - p_{1c1,j}| \qquad (20)$$

<1-2. Control System>

Figure 5:
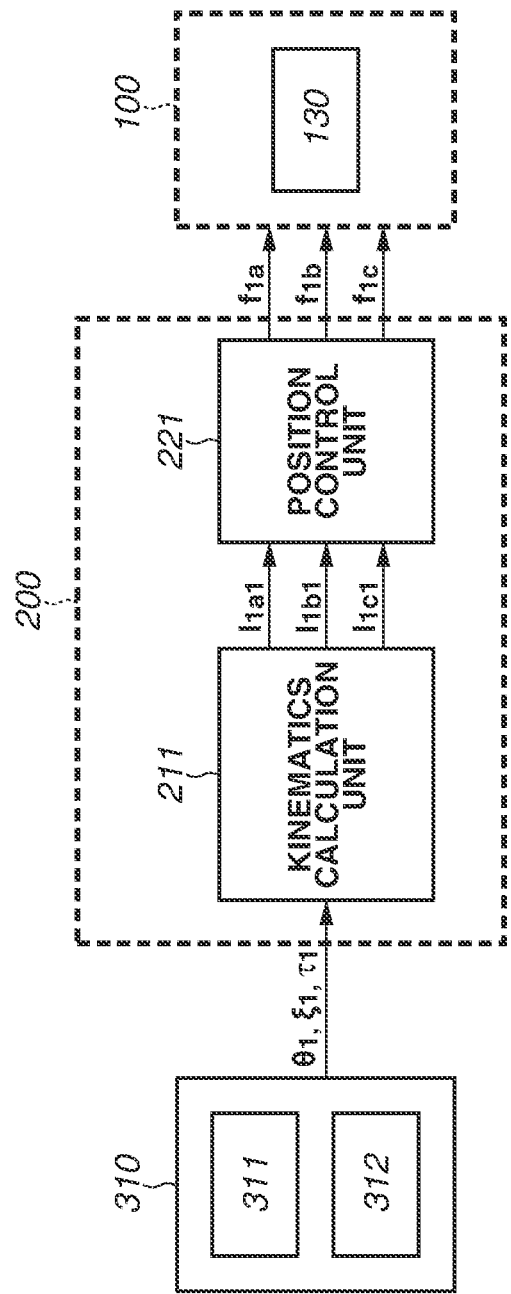
FIG. 5 is a block diagram illustrating an example of a functional configuration of a continuum robot control system according to the first exemplary embodiment.

FIG. 5 is a block diagram illustrating an example of a functional configuration of a continuum robot control system 10 according to the present exemplary embodiment. The continuum robot control system 10 according to the present exemplary embodiment is hereinafter referred to as a "continuum robot control system 10-1". In FIG. 5, components similar to those illustrated in FIGS. 1 and 3 are denoted by the same reference numerals and the detailed descriptions thereof will be omitted.

As illustrated in FIG. 5, the continuum robot control system 10-1 includes the continuum robot 100 (more specifically, the continuum robot 100-1 illustrated in FIG. 1), the continuum robot control device 200, and an input device 310. More specifically, the continuum robot control system 10-1 is a control system for the continuum robot 100-1 including the bendable portion 110 configured to be bent by the driving of the wires $1a$ to $1c$, and the actuators (drive units) 130-$1a$ to 130-$1c$ configured to drive the wires $1a$ to $1c$, respectively.

The input device 310 inputs information to the continuum robot control device 200, and includes an input unit 311 and a magnetic sensor unit 312. The input unit 311 is a component that inputs the bending angle (target bending angle) $\theta_1$ of the bendable portion 110 and the turning angle (target turning angle) $\zeta_1$ of the bendable portion 110 to the continuum robot control device 200. The magnetic sensor unit 312 is a component that measures the torsional angle $\tau_1$ about the central axis 113 of the bendable portion 110 based on the intensity and attitude of a magnetic field obtained by the sensor coil 1111 provided at the distal end 111 of the bendable portion 110, and inputs the measured torsional angle as the torsional angle $\tau_1$ of the bendable portion 110 to the continuum robot control device 200. In the present exemplary embodiment, the magnetic sensor unit 312 and the sensor coil 1111 constitute a "torsional angle acquisition unit" that acquires the torsional angle $\tau_1$ of the bendable portion 110.

The continuum robot control device 200 controls the continuum robot 100 (more specifically, the continuum robot 100-1 illustrated in FIG. 1) based on the information input from the input device 310, and includes a kinematics calculation unit 211 and a position control unit 221. The kinematics calculation unit 211 is a component that calculates the lengths $l_{1a1}$, $l_{1b1}$, and $l_{1c1}$ of the wires 1a, 1b, and 1c in the bendable portion 110, respectively based on the bending angle $\theta_1$, the turning angle $\zeta_1$, and the torsional angle $\tau_1$ of the bendable portion 110 that are input from the input device 310. The position control unit 221 is a component that outputs drive commands $f_{1a}$, $f_{1b}$, and $f_{1c}$ to the actuators 130-1a, 130-1b, and 130-1c in the continuum robot 100-1, respectively so that the lengths of the wires 1a, 1b, and 1c in the bendable portion 110 match the lengths $l_{1a1}$, $l_{1b1}$, and $l_{1c1}$, respectively. In other words, the position control unit 221 controls the actuators 130-1a to 130-1c to drive the wires 1a to 1c, based on the lengths $l_{1a1}$ to $l_{1c1}$ of the wires 1a to 1c in the bendable portion 110, respectively, which are obtained by the kinematics calculation unit 211.

Figure 6:
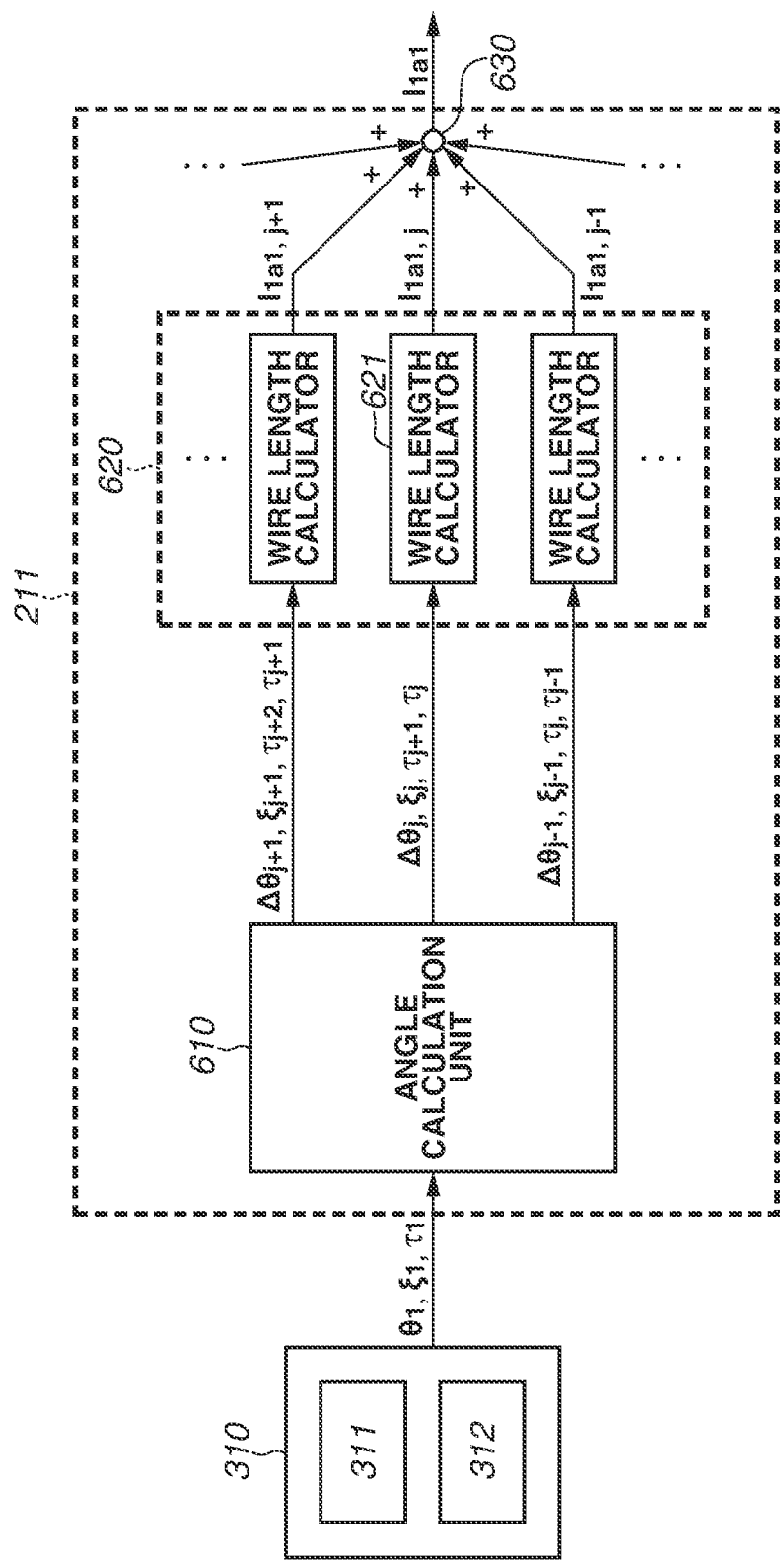
FIG. 6 is a block diagram illustrating an example of a functional configuration of a kinematics calculation unit illustrated in FIG. 5 according to the first exemplary embodiment.

FIG. 6 is a block diagram illustrating an example of a functional configuration of the kinematics calculation unit 211 illustrated in FIG. 5 according to the present exemplary embodiment. In FIG. 6, components similar to those illustrated in FIG. 5 are denoted by the same reference numerals and the detailed descriptions thereof will be omitted. FIG. 6 illustrates a configuration example in which only the length $l_{1a1}$ of the wire 1a, among those of the wires 1a to 1c for bending the bendable portion 110, is calculated. However, in the kinematics calculation unit 211, components similar to those for the wire 1a are also included for the wires 1b and 1c.

As illustrated in FIG. 6, the kinematics calculation unit 211 includes an angle calculation unit 610, a wire length calculation unit 620, and an addition unit 630.

The angle calculation unit 610 calculates, for each of a plurality of minute sections obtained by dividing the bendable portion 110 in the longitudinal direction as described above with reference to FIG. 3, a bending angle $\Delta\theta$, a turning angle $\zeta$, and a torsional angle $\tau$ of the minute section, based on the bending angle $\theta_1$, the turning angle $\zeta_1$, and the torsional angle $\tau_1$ of the bendable portion 110 that are input from the input device 310. More specifically, FIG. 6 illustrates the bending angle $\Delta\theta$, the turning angle $\zeta$, and the torsional angle $\tau$ (including the torsional angle at one end and the torsional angle at the other end) of each of the (j−1)-th minute section, the j-th minute section, and the (j+1)-th minute section, which are calculated by the angle calculation unit 610. In the present exemplary embodiment, the angle calculation unit 610 calculates the bending angle $\Delta\theta_{1,j}$, the turning angle $\zeta_{1,j}$, and the torsional angle $\tau_{1,j}$ of each minute section by using the expressions (5) to (7).

The wire length calculation unit 620 calculates, for each of the plurality of minute sections obtained by dividing the bendable portion 110 in the longitudinal direction, the length $l_{1a1}$ ($l_{1a1,j-1}$, $l_{1a1,j}$, $l_{1a1,j+1}$, and . . .) of the wire 1a in the minute section, based on the bending angle $\Delta\theta$, the turning angle $\zeta$, and the torsional angle $\tau$ of the minute section. More specifically, the wire length calculation unit 620 calculates the lengths $l_{1a1,j-1}$, $l_{1a1,j}$, $l_{1a1,j+1}$, and . . . of the wire 1a in the respective minute sections based on the bending angle $\Delta\theta$, the turning angle $\zeta$, and the torsional angle $\tau$ of each of the minute sections, which are obtained by the angle calculation unit 610. In this case, the wire length calculation unit 620 illustrated in FIG. 6 includes a plurality of wire length calculators 621 each corresponding to a different one of the plurality of minute sections. In the present exemplary embodiment, the wire length calculation unit 620 calculates the length $l_{1a1,j}$ of the wire 1a in the j-th minute section by using the expressions (1) to (4) and the expressions (8) to (11).

The addition unit 630 calculates the length $l_{1a1}$ of the wire 1a in the bendable portion 110 by adding the lengths $l_{1a1,j-1}$, $l_{1a1,j}$, $l_{1a1,j+1}$, and . . . of the wire 1a in the respective minute sections, which are obtained by the wire length calculation unit 620. In the present exemplary embodiment, the addition unit 630 calculates the length $l_{1a1}$ of the wire 1a in the bendable portion 110 (i.e., the length of the wire 1a that passes through the bendable portion 110) by using the expression (12).

<1-3. Simulation>

A simulation has been performed using the model for the continuum robot 100-1 derived in the above-described <1-1. Modeling>, and using the continuum robot control system 10-1 presented in the above-described <1-2. Control System>. In the present exemplary embodiment, it is assumed that the number $m_1$ of minute sections is 20, the length $l_{10}$ of the bendable portion 110 is 0.03 m, and the distance $r_g$ from the central axis 113 of the bendable portion 110 to each of the wires 1a to 1c is 0.002 m.

First, the reason that the length of each of the wires 1a to 1c in the bendable portion 110 can be accurately calculated by application of the continuum robot control system 10-1 according to the present exemplary embodiment even when the bendable portion 110 of the continuum robot 100-1 is twisted will be described.

Figure 7:
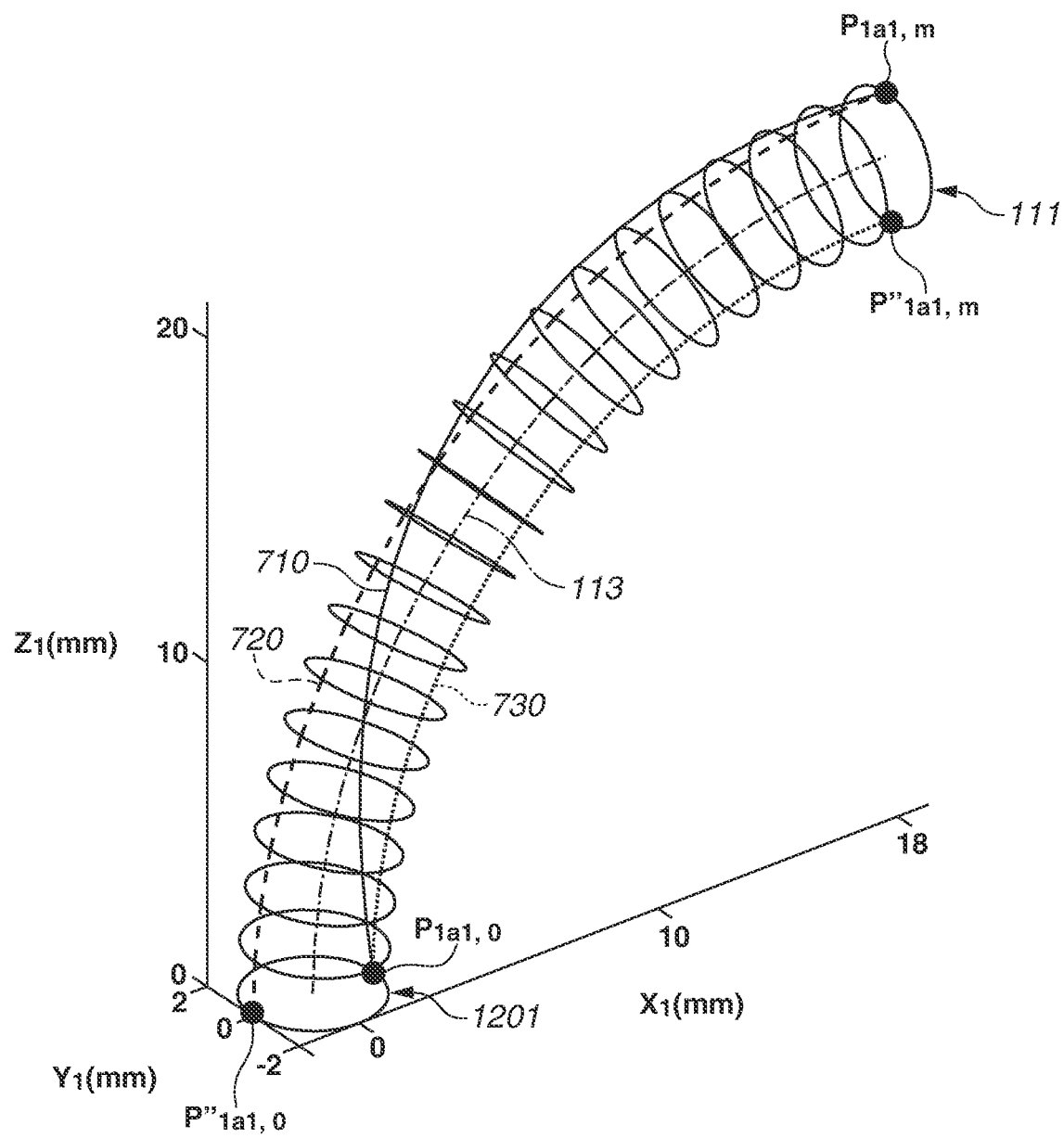
FIG. 7 is a diagram illustrating a result of a simulation using the continuum robot control system according to the first exemplary embodiment.

FIG. 7 illustrates a result of the simulation using the continuum robot control system 10-1 according to the present exemplary embodiment. More specifically, FIG. 7 illustrates a model for the bendable portion 110 assuming that the bending angle $\theta_1$ of the bendable portion 110 is 90 degrees, the turning angle $\zeta_1$ of the bendable portion 110 is 0 degree, and the torsional angle $\tau_1$ of the bendable portion 110 is 180 degrees.

In FIG. 7, the shape of a wire 710 (hereinafter referred to as the "wire 710 according to the present exemplary embodiment") derived using the model for the continuum robot control system 10-1 according to the present exemplary embodiment is indicated by a solid line. As a comparative example, the shape of a wire 720 (hereinafter referred to as the "wire 720 according to Japanese Patent Application Laid-Open No. 2019-122491") derived using a calculation method according to Japanese Patent Application Laid-Open No. 2019-122491 is indicated by a broken line, and the shape of a wire 730 (hereinafter referred to as the "wire 730 not considering a twist") derived without taking into consideration a twist is indicated by a dotted line.

As illustrated in FIG. 7, when the turning angle $\zeta_1$ of the bendable portion 110 is 0 degree and the torsional angle $\tau_1$ of the bendable portion 110 is 180 degrees, a point $P_{1a1,0}$, which is the position of the wire 1a at the front end face 1201 corresponding to the proximal end of the bendable portion 110, is located on the inner periphery of the bendable portion 110. In addition, a point $P_{1a1,m}$, which is the position of the wire 1a at the distal end 111 of the bendable portion 110, is located on the outer periphery of the bendable portion 110. As indicated by the solid line in FIG. 7, the wire 710 according to the present exemplary embodiment moves in a spiral from the point $P_{1a1,0}$ to the point $P_{1a1,m}$ along the central axis 113 of the bendable portion 110. On the other hand, in the case of the wire 720 according to Japanese Patent Application Laid-Open No. 2019-122491, the position of the wire 1a at the front end face 1201 corresponding to the proximal end of the bendable portion 110 corresponds to a point $P'''_{1a1,0}$ obtained by rotating the point $P_{1a1,0}$ about the $Z_1$-axis by the torsional angle $\tau_1$ of 180 degrees. Accordingly, as indicated by the broken line in FIG. 7, the wire 720 according to Japanese Patent Application Laid-Open No. 2019-122491 moves from the point $P'''_{1a1,0}$ to the point $P_{1a1,m}$ on the outer periphery of the bendable portion 110 along the central axis 113 of the bendable portion 110. In the case of the wire 730 not considering a twist, the position of the wire 1a at the distal end 111 of the bendable portion 110 corresponds to a point $P'''_{1a1,m}$ obtained by rotating the point $P_{1a1,m}$ about a $Z_{1,m+1}$-axis by minus 180 degrees. Accordingly, as indicated by the dotted line in FIG. 7, the wire 730 not considering a twist moves from the point $P_{1a1,0}$ to the point $P'''_{1a1,m}$ on the inner periphery of the bendable portion 110 along the central axis 113 of the bendable portion 110.

Figure 8:
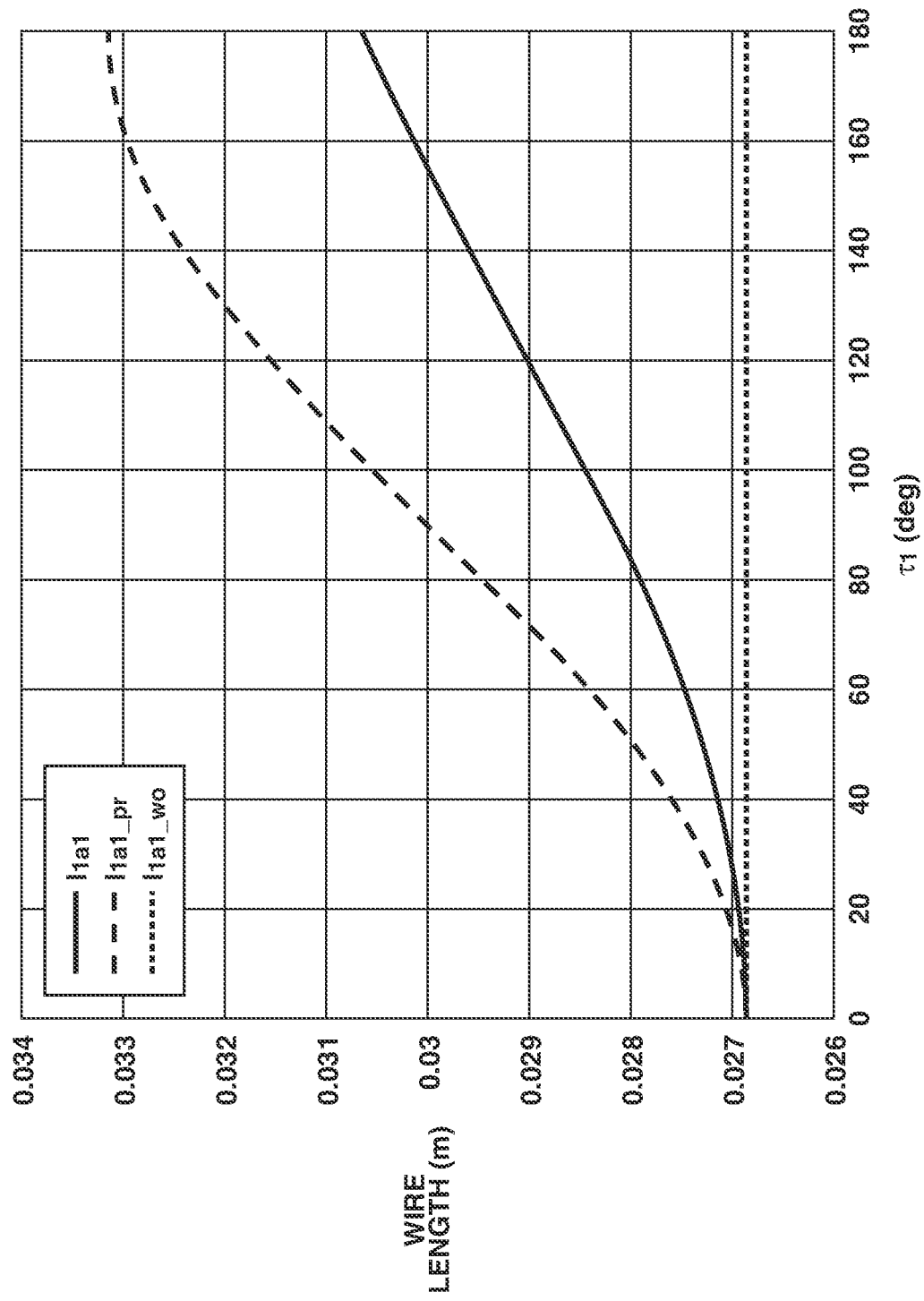
FIG. 8 is a graph illustrating the result of the simulation using the continuum robot control system according to the first exemplary embodiment.

FIG. 8 is a graph illustrating the result of the simulation using the continuum robot control system 10 according to the present exemplary embodiment. More specifically, FIG. 8 illustrates how the length $l_{1a1}$ of the wire 1a changes when the bending angle $\theta_1$ of the bendable portion 110 is 90 degrees, the turning angle $\zeta_1$ of the bendable portion 110 is 0 degree, and the torsional angle $\tau_1$ of the bendable portion 110 is changed from 0 to 180 degrees.

As illustrated in FIG. 8, the length $l_{1a1}$ of the wire 710 according to the present exemplary embodiment illustrated in FIG. 7 is indicated by a solid line, a length $l_{1a1\_pr}$ of the wire 720 according to Japanese Patent Application Laid-Open No. 2019-122491 illustrated in FIG. 7 is indicated by a broken line, and a length $l_{1a1\_wo}$ of the wire 730 not considering a twist illustrated in FIG. 7 is indicated by a dotted line. As indicated by the solid line in FIG. 8, the length $l_{1a1}$ of the wire 710 according to the present exemplary embodiment increases as the torsional angle $\tau_1$ increases because the pitch of the spiral decreases. As indicated by the broken line in FIG. 8, when the torsional angle $\tau_1$ is in a range from 0 to 180 degrees, the wire 720 according to Japanese Patent Application Laid-Open No. 2019-122491 moves on the outer peripheral of the bendable portion 110 more than the wire 710 according to the present exemplary embodiment, and thus the length $l_{1a1\_pr}$ of the wire 720 according to Japanese Patent Application Laid-Open No. 2019-122491 is longer than the length $l_{1a1}$ of the wire 710 according to the present exemplary embodiment. Furthermore, as indicated by the dotted line in FIG. 8, the wire 730 not considering a twist moves on the inner periphery of the bendable portion 110 regardless of the torsional angle $\tau_1$, and thus the length $l_{1a1\_wo}$ of the wire 730 is shorter than the length $l_{1a1}$ of the wire 710 according to the present exemplary embodiment.

In the continuum robot control system 10-1 according to the present exemplary embodiment, the wire length calculation unit 620 calculates the lengths $l_{1a1,j-1}$, $l_{1a1,j}$, $l_{1a1,j+1}$, and . . . of the wire 1a in the respective plurality of minute sections obtained by dividing the bendable portion 110 in the longitudinal direction, based on the bending angle $\Delta\theta$, the turning angle $\zeta$, and the torsional angle $\tau$ of each of the plurality of minute sections. Then, the addition unit 630 calculates the length $l_{1a1}$ of the wire 1a in the bendable portion 110 by adding the lengths $l_{1a1,j-1}$, $l_{1a1,j}$, $l_{1a1,j+1}$, and . . . of the wire 1a in the respective minute sections, which are obtained by the wire length calculation unit 620.

With the above-described configuration, even when the bendable portion 110 of the continuum robot 100-1 is twisted, the length $l_{1a1}$ of the wire 1a in the bendable portion 110 can be accurately calculated. Processing similar to that for the wire 1a is performed on the other wires 1b and 1c for bending the bendable portion 110, thereby making it possible to accurately calculate the length $l_{1b1}$ of the wire 1b and the length $l_{1c1}$ of the wire 1c in the bendable portion 110 even when the bendable portion 110 is twisted. As a result, an improvement in the control performance of the continuum robot 100-1 can be achieved. Furthermore, the above-described configuration of the continuum robot control system 10-1 according to the present exemplary embodiment makes it possible to reduce an error between the target attitude of the bendable portion 110 and the actual attitude of the bendable portion 110 even when the bendable portion 110 is twisted, which leads to an improvement in the safety and operability of the bendable portion 110.

Next, a second exemplary embodiment of the present disclosure will be described. In the present exemplary embodiment, descriptions of components in common with those according to the first exemplary embodiment will be omitted, and only differences from the first exemplary embodiment will be described.

<2-1. Modeling>

While in the first exemplary embodiment, the configuration in which the continuum robot 100-1 includes the single bendable portion 110 configured to be bent three-dimensionally has been assumed and described, in the present exemplary embodiment, a configuration in which the continuum robot 100 includes a plurality of the bendable portions 110 (two bendable portions 110-1 and 110-2) will be assumed and described.

Figure 9:
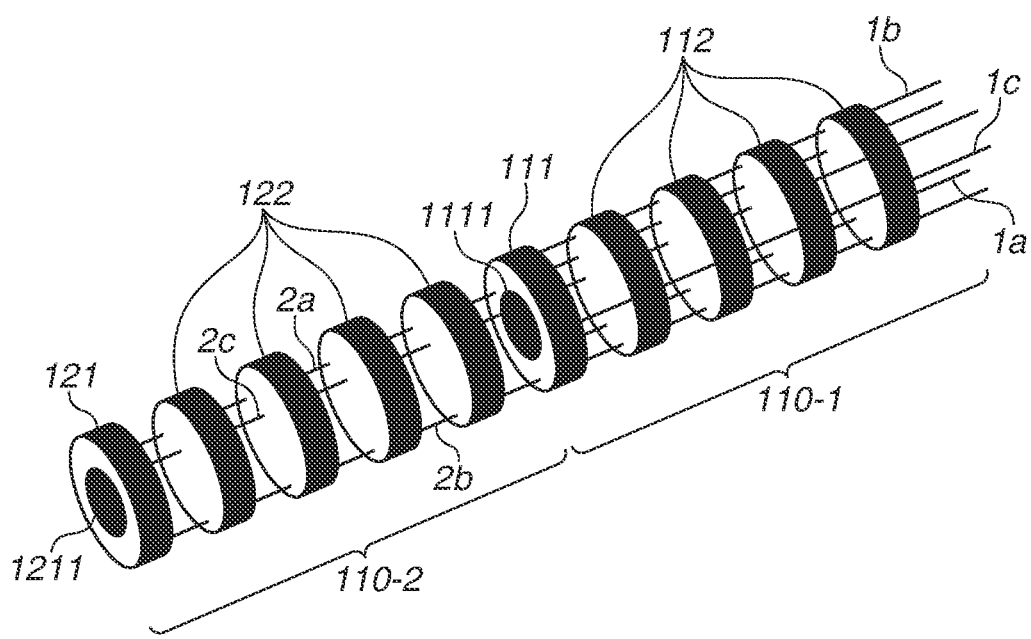
FIG. 9 is a diagram illustrating an example of an external configuration of a continuum robot used in a second exemplary embodiment of the present disclosure.

FIG. 9 illustrates an example of an external configuration of the continuum robot 100 used in the present exemplary embodiment. The continuum robot 100 according to the present exemplary embodiment is hereinafter referred to as a "continuum robot 100-2". In FIG. 9, components similar to those illustrated in FIGS. 1 and 2 are denoted by the same reference numerals. FIG. 9 illustrates only the two bendable portions 110-1 and 110-2 in the continuum robot 100-2 used in the present exemplary embodiment. In other words, the continuum robot 100-2 used in the present exemplary embodiment includes not only the two bendable portions 110-1 and 110-2 illustrated in FIG. 9, but also components corresponding to the long portion 120 and the actuators 130 illustrated in FIG. 1.

More specifically, the continuum robot 100-2 illustrated in FIG. 9 includes the first bendable portion 110-1 and the second bendable portion 110-2 as a plurality of bendable portions arranged in series. The first bendable portion 110-1 corresponds to the bendable portion 110 illustrated in FIGS. 1 and 2. The second bendable portion 110-2 is provided at a position farther from the actuators 130 serving as drive units than the first bendable portion 110-1. While in the present exemplary embodiment, the example where two bendable portions, i.e., the first bendable portion 110-1 and the second bendable portion 110-2 are included as the plurality of bendable portions is illustrated, a configuration including three or more bendable portions can also be used.

The first bendable portion 110-1 is a component configured to be bent three-dimensionally by the driving of at least one of the wires 1a to 1c. The distal end 111 of the first bendable portion 110-1 is provided with the small sensor coil 1111 for detecting the torsional angle $\tau_1$ indicating the torsional amount about the central axis 113 of the first bendable portion 110-1. The wires 1a to 1c illustrated in FIG. 9 are guided by the plurality of wire guides 112 illustrated in FIG. 9 and the hole formed in the long portion 120 illustrated in FIG. 1. In the present exemplary embodiment, it is assumed that the first bendable portion 110-1 ranges from the proximal end corresponding to the front end face 1201 of the long portion 120 illustrated in FIG. 1 to the distal end 111 at which the sensor coil 1111 is provided. The wires 1a to 1c illustrated in FIG. 9 each have one end that is connected to the distal end 111 (the wire guide provided with the sensor coil 1111) of the first bendable portion 110-1 illustrated in FIG. 9, and the other end that is connected to the corresponding one of the actuators 130-1a to 130-1c illustrated in FIG. 1. In the present exemplary embodiment, when the actuators 130-1a to 130-1c are driven in the central axis direction of the first bendable portion 110-1, the wires 1a to 1c are each pushed or pulled, thereby enabling the first bendable portion 110-1 to be bent three-dimensionally.

The second bendable portion 110-2 is a component configured to be bent three-dimensionally by driving of at least one of wires 2a, 2b, and 2c. A distal end 121 of the second bendable portion 110-2 is provided with a small sensor coil 1211 for detecting a torsional angle 12 indicating a torsional amount about a central axis of the second bendable portion 110-1. The wires 2a to 2c illustrated in FIG. 9 are guided by a plurality of wire guides 122 illustrated in FIG. 9, the distal end 11I and the plurality of wire guides 112 of the first bendable portion 110-1, and the hole formed in the long portion 120 illustrated in FIG. 1. In other words, in the present exemplary embodiment, the distal end 11I and the plurality of wire guides 112 of the first bendable portion 110-1 are provided with not only holes for guiding the wires 1a to 1c, but also holes for guiding the wires 2a to 2c. In the present exemplary embodiment, it is assumed that the second bendable portion 110-2 ranges from the proximal end corresponding to the distal end 11I of the first bendable portion 110-1 illustrated in FIG. 9 to the distal end 121 provided with the sensor coil 1211. The wires 2a to 2c illustrated in FIG. 9 each have one end that is connected to the distal end 121 (the wire guide provided with the sensor coil 1211) of the second bendable portion 110-2 illustrated in FIG. 9, and the other end that is connected to the corresponding one of actuator 130-2a to 130-2c (not illustrated) that correspond to the actuators 130-1a to 130-1c illustrated in FIG. 1, respectively. In the present exemplary embodiment, when the actuators 130-2a to 130-2c (not illustrated) are driven in the central axis direction of the second bendable portion 110-2, the wires 2a to 2c are each pushed or pulled, thereby enabling the second bendable portion 110-2 to be bent three-dimensionally.

Figure 10:
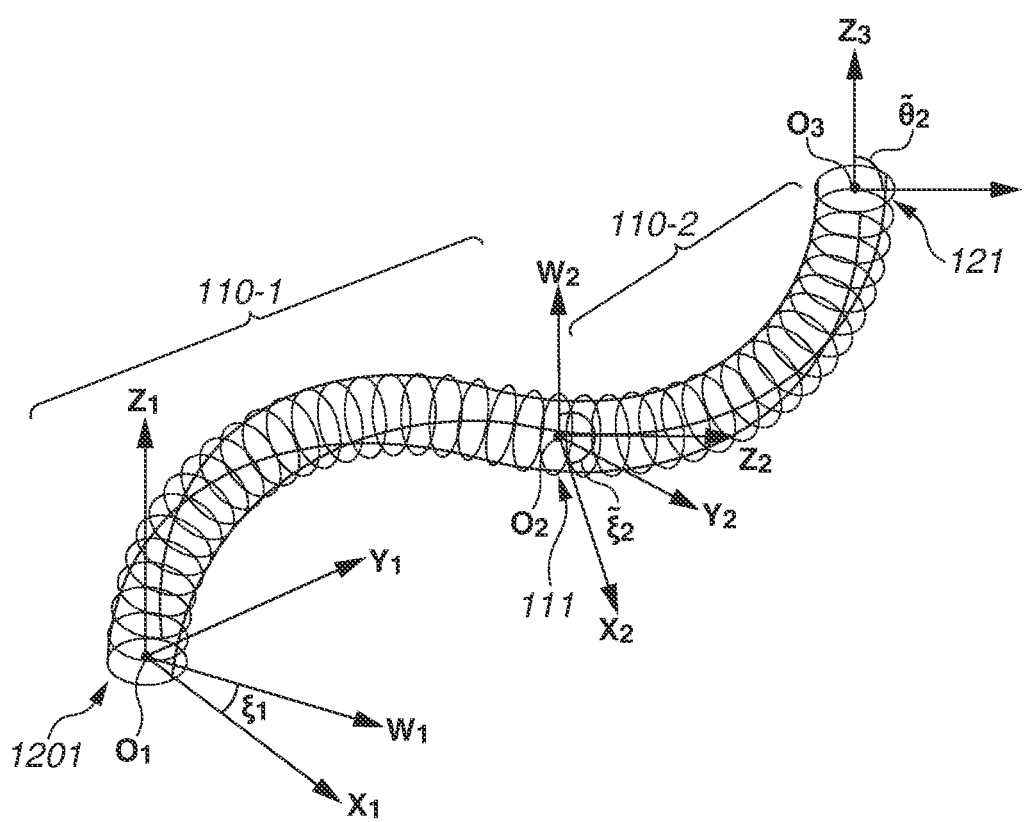
FIG. 10 is a diagram illustrating an example of a model for each of a first bendable portion and a second bendable portion illustrated in FIG. 9.

FIG. 10 illustrates an example of a model for each of the first bendable portion 110-1 and the second bendable portion 110-2 illustrated in FIG. 9. In FIG. 10, components similar to those illustrated in FIGS. 3 and 9 are denoted by the same reference numerals and the detailed descriptions thereof will be omitted.

As illustrated in FIG. 10, the distal end 111 of the first bendable portion 110-1 is defined as an origin $O_2$, the $Z_2$-axis is provided in the normal direction to the distal end 111, an $X_2$-axis is provided in a circumferential direction, and a $Y_2$-axis is provided in the direction orthogonal to each of the $X_2$-axis and the $Z_2$-axis. Furthermore, a $W_2$-axis is provided in the direction from the origin $O_2$ to a central point $O_3$ of the distal end 121 of the second bendable portion 110-2 within an $X_2$-$Y_2$ plane, and an angle formed between the $X_2$-axis and the $W_2$-axis is defined as a turning angle $\sim\zeta_2$ of the second bendable portion 110-2. In this example, the symbol "$\sim$" used for the turning angle $\sim\zeta_2$ of the second bendable portion 110-2 indicates a relative coordinate system. In the following mathematical expressions, the reference symbol ($\sim$) indicating a relative coordinate system is added to the top of each element. However, in the following description, the reference symbol ($\sim$) is added to the side of each element, for example, like the turning angle "$\sim\zeta_2$", because of the format. The reference symbol ($\sim$) added to the side of each element indicates the same meaning as the reference symbol ($\sim$) added to the top of each element.

In FIG. 10, the central point $O_3$ of the distal end 121 of the second bendable portion 110-2 is defined as an origin, and a $Z_3$-axis is provided in the normal direction to the distal end 121. Furthermore, an angle formed between the $Z_2$-axis and the $Z_3$-axis is defined as a relative bending angle $\sim\theta_2$ of the second bendable portion 110-2 relative to the first bendable portion 110-1.

According to the present exemplary embodiment, in the wire 2a, a length $l_{2a1}$ of a portion that passes through the first bendable portion 110-1 and a length $l_{2a2}$ of a portion that passes through the second bendable portion 110-2 are calculated using a method similar to that used in the first exemplary embodiment. In the present exemplary embodiment, an overall length $l_{2a}$ of the wire 2a in the first bendable portion 110-1 and the second bendable portion 110-2 is calculated by adding the length $l_{2a1}$ and the length $l_{2a2}$.

First, the length $l_{2a1}$ of the wire 2a in the first bendable portion 110-1 (i.e., the length of the wire 2a that passes through the first bendable portion 110-1) is derived. A length $l_{2a1,j}$ of the wire 2a in the j-th minute section of the first bendable portion 110-1 corresponds to the difference between a vector $p_{2a1,j}$ from the origin $O_{1,j}$ to the front end face 1201 corresponding to the proximal end and a vector $p_{2a1,j+1}$ from the origin $O_{1,j}$ to the distal end 111. Accordingly, similarly to the expression (11) according to the first exemplary embodiment, the length $l_{2a1,j}$ is represented by the following expression (21).

$$l_{2a1,j} = |p_{2a1,j+1} - p_{2a1,j}| \tag{21}$$

Assuming that the phase of the wire 2a with respect to the wire 1a is represented by $\xi_2$, the vector $p_{2a1,j}$ is represented by the following expression (22), similarly to the expression (1).

$$p_{2a1,j} = [r_g \cos(\tau_{1,j} + \xi_2) r_g \sin(\tau_{1,j} + \xi_2) 0]^T \tag{22}$$

Similarly to the expression (8), the vector $p_{2a1,j+1}$ is represented by the following expression (23) using a vector $p'_{2a1,j}$ from the origin $O_{1,j}$ to a point $P'_{2a1,j}$ obtained by projecting a point $P_{2a1,j+1}$ onto the $X_{1,j}$-$Y_{1,j}$ plane.

$$p_{2a1,j+1} = R_z(\zeta_{1,j}) R_y(\Delta\theta_{1,j}) R_z(-\zeta_{1,j})(p'_{2a1,j} - t_{1,j}) + t_{1,j} \tag{23}$$

Similarly to the expression (2), the vector $p'_{2a1,j}$ is represented by the following expression (24).

$$p'_{2a1,j} = [r_g \cos(\tau_{1,j+1} + \xi_2) r_g \sin(\tau_{1,j+1} + \xi_2) 0]^T \tag{24}$$

The length $l_{2a1}$ is obtained by adding the lengths $l_{2a1,j}$ in all minute sections by using the following expression (25).

$$l_{2a1} = \sum_{j=1}^{m_1} |p_{2a1,j+1} - p_{2a1,j}| \tag{25}$$

Next, the length $l_{2a2}$ of the wire $2a$ in the second bendable portion 110-2 (i.e., the length of the wire $2a$ that passes through the second bendable portion 110-2) is derived. A length $l_{2a2,k}$ of the wire $2a$ in the k-th (k=1, 2, . . . , $m_2$) minute section of the second bendable portion 110-2 corresponds to the difference between a vector $p_{2a2,k}$ from an origin $O_{2,k}$ of the minute section to the proximal end (the distal end 111 of the first bendable portion 110-1) and a vector $p_{2a2,k+1}$ from the origin $O_{2,k}$ to the distal end 121. Accordingly, the length $l_{2a2,k}$ is represented by the following expression (26), similarly to the expression (11).

$$l_{2a2,k}=|p_{2a2,k+1}-p_{2a2,k}| \quad (26)$$

Similarly to the expression (1), the vector $p_{2a2,k}$ is represented by the following expression (27) using a torsional angle $\tau_{2,k}$ of the k-th minute section.

$$p_{2a2,k}=[r_g \cos(\tau_{2,k}+\xi_2) r_g \sin(\tau_{2,k}+\xi_2) O]^T \quad (27)$$

Similarly to the expression (8), the vector $p_{2a2,k+1}$ is represented by the following expression (28) using a bending angle $\sim\theta_{2,k}$ and a vector $p'_{2a2,k}$ from the origin $O_{2,k}$ to a point $P'_{2a2,k}$ obtained by projecting a point $P_{2a2,k+1}$ onto an $X_{2,k}$—$Y_{2,k}$ plane.

$$p_{2a2,k+1}=R_Z(\zeta_{2,k})R_y(\Delta\tilde{\theta}_{2,k})R_z(-\zeta_{2,k})(p'_{2a2,k}-t_{2,k})+t_{2,k} \quad (28)$$

Similarly to the expression (2), the vector $p'_{2a2,k}$ is represented by the following expression (29).

$$p'_{2a2,k}=[r_g \cos(\tau_{2,k+1}+\xi_2) r_g \sin(\tau_{2,k+1}+\xi_2) O]^T \quad (29)$$

Similarly to the expressions (3) to (7) according to the first exemplary embodiment, $t_{2,k},\Delta l_{2,k}, \Delta\sim\theta_{2,k}, \sim\zeta_{2,k}$ and $\tau_{2,k}$ are obtained by using the following expressions (30) to (34), respectively, in the present exemplary embodiment.

$$t_{2,k} = \left[\frac{\Delta l_{2,k}}{\Delta\theta_{2,k}}\cos(\zeta_{2,k}) \frac{\Delta l_{2,k}}{\Delta\theta_{2,k}}\sin(\zeta_{2,k}) O\right]^T \quad (30)$$

$$\Delta l_{2,k} = \frac{l_{20}}{m_2} \quad (31)$$

$$\Delta\tilde{\theta}_{2,k} = \frac{\tilde{\theta}_2}{m_2} \quad (32)$$

$$\tilde{\zeta}_{2,k} = \tilde{\zeta}_2 \quad (33)$$

$$\tau_{2,k} = \frac{\tau_2}{m_2}(k-1) \quad (34)$$

The length $l_{2a2}$ is obtained by adding the lengths $l_{2a2,k}$ in all minute sections by using the following expression (35).

$$l_{2a2} = \sum_{k=1}^{m_2} |p_{2a2,k+1} - p_{2a2,k}| \quad (35)$$

The overall length $l_{2a}$ of the wire $2a$ in the first bendable portion 110-1 and the second bendable portion 110-2 is calculated by using the following expression (36).

$$l_{2a}=l_{2a1}+l_{2a2} \quad (36)$$

Similarly to the case of the wire $2a$, also for each of the other wires $2b$ and $2c$, the length of a portion that passes through the first bendable portion 110-1 and the length of a portion that passes through the second bendable portion 110-2 are calculated separately and added together, so that the overall length $l_{2b}$ of the wire $2b$ and the overall length $l_{2c}$ of the wire $2c$ in the first bendable portion 110-1 and the second bendable portion 110-2 can be calculated.

<2-2. Control System>

Figure 11:
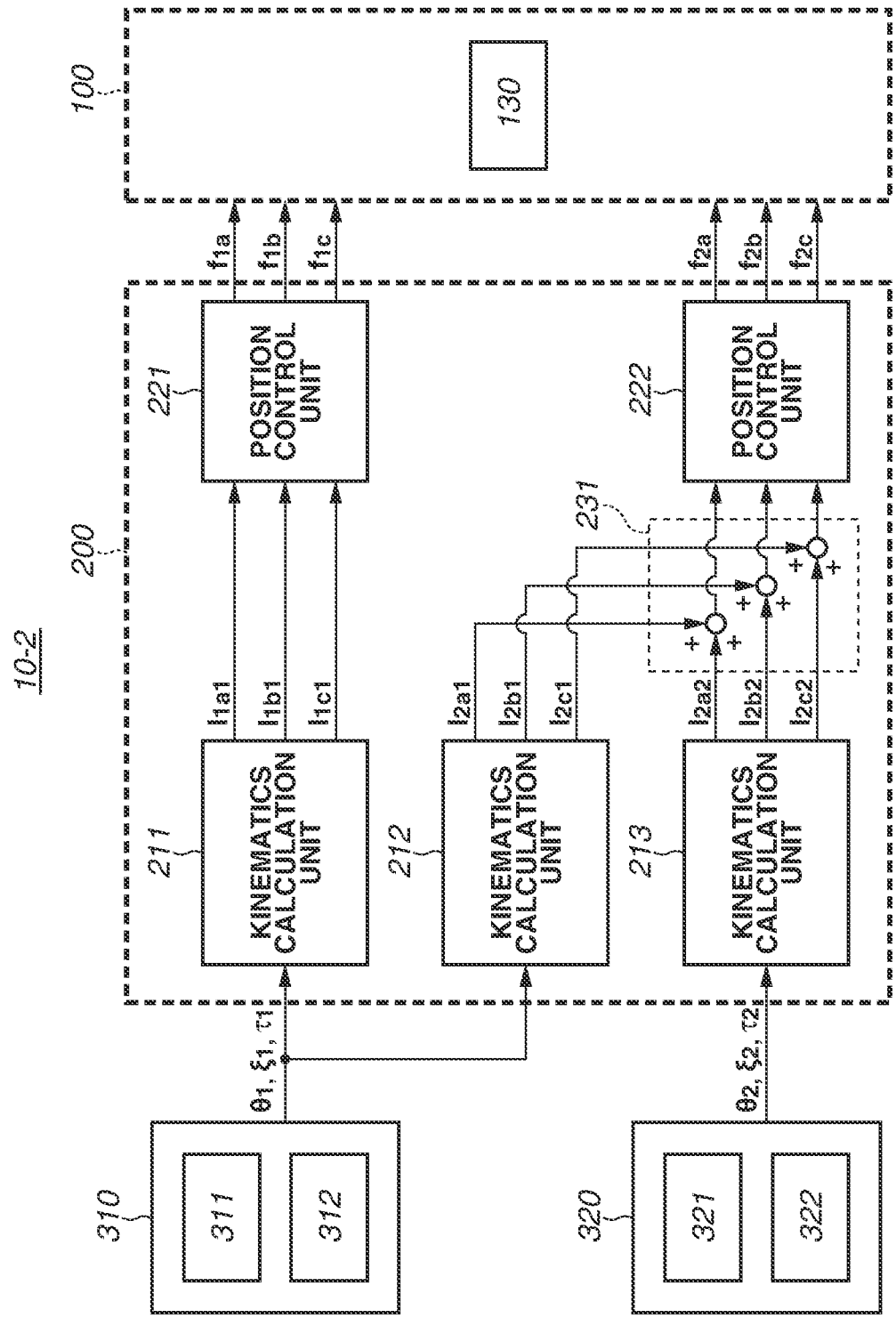
FIG. 11 is a block diagram illustrating an example of a functional configuration of a continuum robot control system according to the second exemplary embodiment.

FIG. 11 is a block diagram illustrating an example of a functional configuration of the continuum robot control system 10 according to the present exemplary embodiment. The continuum robot control system 10 according to the present exemplary embodiment is hereinafter referred to as a "continuum robot control system 10-2". In FIG. 11, components similar to those illustrated in FIGS. 5 and 10 are denoted by the same reference numerals and the detailed descriptions thereof will be omitted.

As illustrated in FIG. 11, the continuum robot control system 10-2 includes the continuum robot 100 (more specifically, the continuum robot 100-2 illustrated in FIG. 9), the continuum robot control device 200, the input device 310, and an input device 320. More specifically, the continuum robot control system 10-2 is a control system for the continuum robot 100-2 including the first bendable portion 110-1 configured to be bent by the driving of the wires $1a$ to $1c$, the second bendable portion 110-2 configured to be bent by the driving of the wires $2a$ to $2c$, the actuators (drive units) 130-1$a$ to 130-1$c$ configured to drive the wires $1a$ to $1c$, respectively, and the actuators (drive units) 130-2$a$ to 130-2$c$ configured to drive the wires $2a$ to $2c$, respectively.

The continuum robot control system 10-2 illustrated in FIG. 11 has a configuration in which the input device 320 is added to the continuum robot control system 10-1 illustrated in FIG. 5.

The input unit 311 of the input device 310 is a component that inputs the bending angle (target bending angle) $\theta_1$ of the first bendable portion 110-1 and the turning angle (target turning angle) $\zeta_1$ of the first bendable portion 110-1 to the continuum robot control device 200. The magnetic sensor unit 312 of the input device 310 is a component that measures the torsional angle $\tau_1$ about the central axis 113 of the first bendable portion 110-1 based on the intensity and attitude of a magnetic field obtained by the sensor coil 1111 provided at the distal end 111 of the first bendable portion 110-1, and inputs the measured torsional angle as the torsional angle $\tau_1$ of the first bendable portion 110-1 to the continuum robot control device 200. In the present exemplary embodiment, the magnetic sensor unit 312 and the sensor coil 1111 constitute the "torsional angle acquisition unit" that acquires the torsional angle $\tau_1$ of the bendable portion 110.

The input device 320 inputs information to the continuum robot control device 200, and includes an input unit 321 and a magnetic sensor unit 322. The input unit 321 is a component that inputs a bending angle (target bending angle) $\theta_2$ of the second bendable portion 110-2 and a turning angle (target turning angle) $\zeta_2$ of the second bendable portion 110-2 to the continuum robot control device 200. The magnetic sensor unit 322 is a component that measures the torsional angle $\tau_2$ about the central axis 113 of the second bendable portion 110-2 based on the intensity and attitude of a magnetic field obtained by the sensor coil 1211 provided at the distal end 121 of the second bendable portion 110-2, and inputs the measured torsional angle as the torsional angle $\tau_2$ of the second bendable portion 110-2 to the continuum robot control device 200. In the present exemplary embodiment, the magnetic sensor unit 322 and the sensor coil 1211 constitute the "torsional angle acquisition unit" that acquires the torsional angle $\tau_2$ of the bendable portion 110.

The continuum robot control device 200 illustrated in FIG. 11 controls the continuum robot 100 (more specifically, the continuum robot 100-2 illustrated in FIG. 9) based on the information input from the input device 310 and the input device 320. The continuum robot control device 200 illustrated in FIG. 11 includes kinematics calculation units 211 to 213, position control units 221 to 222, and an addition unit 231. The kinematics calculation unit 211 and the position control unit 221 illustrated in FIG. 11 perform processing similar to that performed by the kinematics calculation unit 211 and the position control unit 221 illustrated in FIG. 5, respectively, and thus the descriptions thereof will be omitted.

The kinematics calculation unit 212 is a component that calculates lengths $l_{2a1}$, $l_{2b1}$, and $l_{2c1}$ of the wires 2a, 2b, and 2c in the first bendable portion 110-1 by using the expression (25), respectively, based on the bending angle $\theta_1$, the turning angle $\zeta_1$, and the torsional angle $\tau_1$ of the first bendable portion 110-1 that are information input from the input device 310. The kinematics calculation unit 213 is a component that calculates lengths $l_{2a2}$, $l_{2b2}$, and $l_{2c2}$ of the wires 2a, 2b, and 2c in the second bendable portion 110-2 by using the expression (35), respectively, based on the bending angle $\theta_2$, the turning angle $\zeta_2$, and the torsional angle $\tau_2$ of the second bendable portion 110-2 that are information input from the input device 320.

The addition unit 231 calculates the overall lengths $l_{2a}$ to $l_{2c}$ of the wires 2a to 2c in the first bendable portion 110-1 and the second bendable portion 110-2, respectively by adding the lengths $l_{2a1}$, $l_{2b1}$, and $l_{2c1}$ of the wires 2a, 2b, and 2c in the first bendable portion 110-1 calculated by the kinematics calculation unit 212 and the lengths $l_{2a2}$, $l_{2b2}$, and $l_{2c2}$ of the wires 2a, 2b, and 2c in the second bendable portion 110-2 calculated by the kinematics calculation unit 213, respectively.

The position control unit 222 is a component that outputs drive commands $f_{2a}$, $f_{2b}$, and $f_{2c}$ to the actuators 130-2a, 130-2b, and 130-2c of the continuum robot 100-2, respectively so that the lengths of the wires 2a, 2b, and 2c in the second bendable portion 110-2 match the lengths $l_{2a}$, $l_{2b}$, and $l_{2c}$ calculated by the addition unit 231, respectively. In other words, the position control unit 222 controls the actuators 130-2a to 130-2c to drive the wires 2a to 2c, respectively, based on the lengths $l_{2a1}$, $l_{2b1}$, and $l_{2c1}$ of the wires 2a, 2b, and 2c in the first bendable portion 110-1 and the lengths $l_{2a2}$, $l_{2b2}$, and $l_{2c2}$ of the wires 2a, 2b, and 2c in the second bendable portion 110-2, which are obtained by the kinematics calculation unit 212 and the kinematics calculation unit 213.

While in the present exemplary embodiment, the example where the continuum robot 100-2 includes the two bendable portions 110-1 and 110-2 has been assumed and described, in general, a continuum robot including "n" (three or more) bendable portions may also be used similarly. More specifically, the overall length of each wire for bending the i-th (i=1, 2, . . . , n) bendable portion is derived using "i" kinematics calculation units configured to calculate the respective lengths of the wire in the first to the i-th bendable portions, and using an addition unit configured to add the lengths output therefrom.

According to the present exemplary embodiment, even when the plurality of bendable portions 110 of the continuum robot 100-2 is twisted, the length of each wire in each of the plurality of bendable portions 110 can be accurately calculated. Thus, an improvement in the control performance of the continuum robot 100-2 can be achieved. Furthermore, even when the plurality of bendable portions 110 of the continuum robot 100-2 is twisted, it is possible to reduce an error between the target attitude and the actual attitude of each of the plurality of bendable portions 110, which leads to an improvement in the safety and operability of the bendable portions 110.

Next, a third exemplary embodiment of the present disclosure will be described. In the present exemplary embodiment, descriptions of components in common with those according to the first and second exemplary embodiments described above will be omitted, and only differences from the first and second exemplary embodiments will be described.

In the present exemplary embodiment, a control system for the continuum robot 100 in which the distribution of each of the bending angle $\theta$, the turning angle $\zeta$, and the torsional angle $\tau$ of the bendable portion 110 is not uniform is applied.

In the first and second exemplary embodiments, as indicated by the expressions (7) and (34), the torsional angle $\tau$ of each minute section is derived assuming that the torsional angle $\tau$ indicating the torsional amount of the bendable portion 110 is uniformly distributed. Similarly, in the first and second exemplary embodiments, as indicated by the expressions (5) and (32), the bending angle $\Delta\theta$ of each minute section is derived assuming that the bendable portion 110 is bent with a constant curvature. However, a path in an organ, such as a large intestine or a lung, is bent in a complicated manner. Accordingly, the above-described assumptions are not always satisfied in the bendable portion 110 that enters into such an organ. In this case, the bending angle $\theta$, the turning angle $\zeta$, and the torsional angle $\tau$ of each minute section are obtained so as to correspond to the shape of the path into which the bendable portion 110 enters, and the length of each wire in the bendable portion 110 is calculated based on the obtained angles, so that the control performance of the continuum robot 100 can be improved. Thus, the control system according to the present exemplary embodiment first stores the bending angle $\theta$, the turning angle $\zeta$, and the torsional angle $\tau$ of when the distal end 111 of the bendable portion 110 of the continuum robot 100 passes through a certain point on a narrow space. Then, when the minute section of the bendable portion 110 reaches the point, the stored angles are read out and used to calculate the length of each wire in the bendable portion 110.

In the following description, only differences from the first exemplary embodiment will be described.

Figure 12:
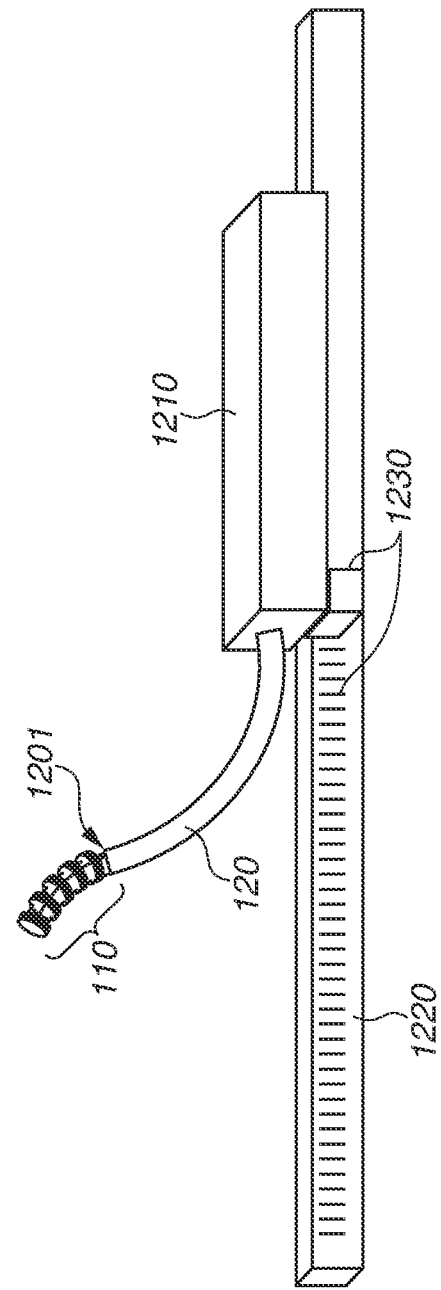
FIG. 12 is a diagram illustrating an example of an external configuration of a continuum robot control system according to a third exemplary embodiment of the present disclosure.

FIG. 12 illustrates an example of an external configuration of the continuum robot control system 10 according to the present exemplary embodiment. The continuum robot control system 10 according to the present exemplary embodiment is hereinafter referred to as a "continuum robot control system 10-3". In FIG. 12, components similar to those illustrated in FIG. 1 are denoted by the same reference numerals and the detailed descriptions thereof will be omitted.

The continuum robot control system 10-3 illustrated in FIG. 12 includes the bendable portion 110, the long portion 120, an actuator/control system built-in box 1210, a direct-acting guide mechanism portion 1220, and a position sensor portion 1230.

The actuator/control system built-in box 1210 is a component that incorporates, for example, the actuators 130-1a to 130-1c illustrated in FIG. 1, and the continuum robot control device 200 and the input device 310 illustrated in FIG. 5.

The direct-acting guide mechanism portion 1220 is a component that guides the actuator/control system built-in box 1210, which is provided with the long portion 120 and the bendable portion 110, in a direct-acting manner. More specifically, the actuator/control system built-in box 1210 moves forward or backward in the longitudinal direction of the bendable portion 110.

The position sensor portion 1230 detects a position $Z_b$ in the forward/backward direction of the bendable portion 110 of the continuum robot 100. More specifically, the position sensor portion 1230 detects a displacement $Z_b$ from an initial position of the bendable portion 110.

The continuum robot control system 10-3 according to the present exemplary embodiment is similar to the continuum robot control system 10-1 according to the first exemplary embodiment illustrated in FIG. 5.

Figure 13:
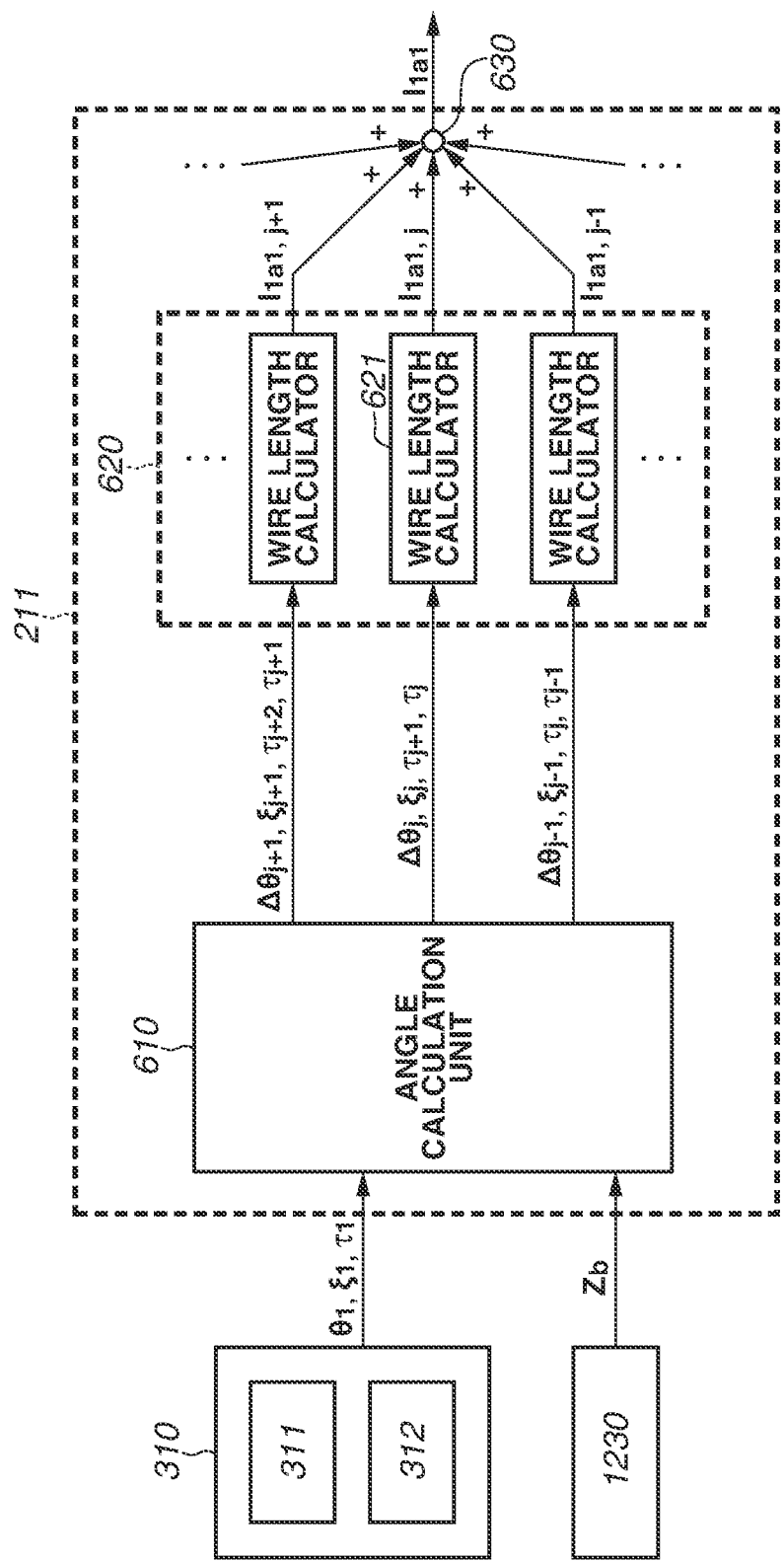
FIG. 13 is a block diagram illustrating an example of a functional configuration of the kinematics calculation unit illustrated in FIG. 5 according to the third exemplary embodiment.

FIG. 13 is a block diagram illustrating an example of a functional configuration of the kinematics calculation unit 211 illustrated in FIG. 5 according to the present exemplary embodiment. In FIG. 13, components similar to those illustrated in FIG. 6 are denoted by the same reference numerals and the detailed descriptions thereof will be omitted.

The kinematics calculation unit 211 according to the present exemplary embodiment illustrated in FIG. 13 differs from the kinematics calculation unit 211 according to the first exemplary embodiment illustrated in FIG. 5 in that the displacement $Z_b$ from the initial position of the bendable portion 110 detected by the position sensor portion 1230 illustrated in FIG. 12 is additionally input to the angle calculation unit 610. More specifically, in the present exemplary embodiment, the angle calculation unit 610 calculates, for each of a plurality of minute sections obtained by dividing the bendable portion 110 in the longitudinal direction, the bending angle $\Delta\theta$, the turning angle $\zeta$, and the torsional angle $\tau$ of the minute section based not only on the bending angle $\theta_1$, the turning angle $\zeta_1$, and the torsional angle $\tau_1$ of the bendable portion 110 that are input from the input device 310, but also on the displacement $Z_b$ from the initial position of the bendable portion 110 detected by the position sensor portion 1230.

When the actuator/control system built-in box 1210 provided with the long portion 120 and the bendable portion 110 moves forward or backward on the direct-acting guide mechanism portion 1220, the angle calculation unit 610 acquires from the position sensor portion 1230 the displacement $Z_b$ from the initial position of the bendable portion 110 and stores the acquired displacement $Z_b$, and also acquires from the input device 310 the bending angle $\theta_1$, the turning angle $\zeta_1$, and the torsional angle $\tau_1$ of the bendable portion 110 corresponding to the displacement $Z_b$, and stores the acquired angles.

When the actuator/control system built-in box 1210 moves to a certain position from the initial position of the direct-acting guide mechanism portion 1220 and the displacement $Z_b$ is detected, a position $Z_{b1,j}$ at the proximal end side of the j-th minute section of the bendable portion 110 is represented by the following expression (37).

$$Z_{b1,j} = Z_b - (m_1 - j + 1)\Delta l_{1,j} \tag{37}$$

Accordingly, the angle calculation unit 610 calculates the bending angle $\Delta\theta_{1,j}$, the turning angle $\zeta_{1,j}$, and the torsional angle $\tau_{1,j}$ of the j-th minute section of the bendable portion 110 by the following expressions (38) to (40).

$$\Delta\theta_{1,j} = \theta_1(Z_{b1,j+1}) - \theta_1(Z_{b1,j}) \tag{38}$$

$$\zeta_{1,j} = \zeta_1(Z_{b1,j}) \tag{39}$$

$$\tau_{1,j} = \tau_1(Z_{b1,j}) \tag{40}$$

With this configuration, the wire length calculation unit 620 can calculate the length of the wire in each minute section based on the bending angle $\Delta\theta$, the turning angle $\zeta$, and the torsional angle $\tau$ of the bendable portion 110 that passes through the position $Z_{b1,j}$ along a narrow space. Therefore, the control performance of the continuum robot 100 can be improved even when the bendable portion 110 enters into a narrow space that is bent in a complicated manner.

While in the present exemplary embodiment, the example where an external force from a narrow space is taken into consideration as a factor for non-uniform distribution of the torsional angle $\tau$ has been described, the length of each wire can also be calculated by taking into consideration factors other than the external force. For example, for the continuum robot 100 in which the torsional rigidity of the bendable portion 110 is non-uniformly distributed, the torsional angle $\tau_{1,j}$ is calculated by using the following expression (41) with a coefficient $\alpha_{1,j}$ corresponding to the torsional rigidity of the j-th minute section, so that the length of each wire can be calculated considering the rigidity distribution.

$$\tau_{1,j} = \alpha_{1,j} \frac{\tau_1}{m_1}(j-1) \tag{41}$$

This can also be applied to the bending angle $\theta$ and the turning angle $\zeta$.

While in the above-described first to third exemplary embodiments, the configuration of the continuum robot control system 10 in which the bending angle, the turning angle, and the torsional angle of the bendable portion 110 are acquired using the input unit and the magnetic sensor unit included in the input device. However, the configuration is not limited thereto. For example, a configuration in which these angles are acquired using a displacement sensor for measuring the amount of deformation of the bendable portion 110 and image information obtained by capturing an image of the shape of the bendable portion 110 may also be used. Alternatively, a configuration in which the bending angle, the turning angle, and the torsional angle of the bendable portion 110 are calculated and acquired based on the shape of a narrow space into which the bendable portion 110 enters may be used.

While in the above-described first to third exemplary embodiments, the configuration where three wires for bending a single bendable portion 110 are pushed or pulled to bend the bendable portion 110 has been described, the configuration is not limited thereto. More specifically, while in the above-described first to third exemplary embodiments, the example of the continuum robot 100 that three-dimensionally drives a single bendable portion 110 has been described, continuum robots to be bent on a plane and continuum robots with a different number of wires may also be used.

The exemplary embodiments of the present disclosure can also be implemented by processing in which a program for implementing one or more functions according to the above-described exemplary embodiments is supplied to a system or an apparatus via a network or a storage medium, and one or more processors in a computer of the system or the apparatus read out and execute the program. The exemplary embodiments can also be implemented by a circuit (e.g., an application specific integrated circuit (ASIC)) for implementing one or more functions according to the above-described exemplary embodiments.

The program and a computer-readable storage medium storing the program are also included in the exemplary embodiments of the present disclosure.

All the above-described exemplary embodiments of the present disclosure merely illustrate examples embodying the present disclosure, and the technical scope of the present disclosure should not be interpreted limitedly by the exemplary embodiments. The present disclosure can be implemented in various forms without departing from the technical idea and main features of the present disclosure.

OTHER EMBODIMENTS

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU), or the like), circuitry, or combinations thereof, and may include a network of separate computers or separate processors to read out and execute the computer executable instructions. The computer executable instructions may be provided to the computer, for example, from a network or the storage medium. The storage medium may include, for example, one or more memories of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2020-128130, filed Jul. 29, 2020, which is hereby incorporated by reference herein in its entirety.

What is claimed is:

1. A control system for a continuum robot including a bendable portion configured to be bent by driving of a wire, and a drive unit configured to drive the wire, the control system comprising:
a torsional angle acquisition unit configured to acquire a torsional angle of the bendable portion; and
a kinematics calculation unit configured to calculate a length of the wire in the bendable portion based on the torsional angle acquired by the torsional angle acquisition unit,
wherein the kinematics calculation unit includes:
a wire length calculation unit configured to calculate, for each of a plurality of minute sections obtained by dividing the bendable portion in a longitudinal direction thereof, a length of the wire in the minute section based on a bending angle, a turning angle, and a torsional angle of the minute section; and
an addition unit configured to add the lengths of the wire in the plurality of minute sections obtained by the wire length calculation unit to calculate the length of the wire in the bendable portion.

2. The control system for the continuum robot according to claim 1, further comprising an angle calculation unit configured to calculate, for each of the plurality of minute sections, the bending angle, the turning angle, and the torsional angle of the minute section, based on a bending angle and a turning angle of the bendable portion and the torsional angle acquired by the torsional angle acquisition unit,
wherein the wire length calculation unit calculates the length of the wire in each of the plurality of minute sections, based on the bending angle, the turning angle, and the torsional angle of the minute section that are obtained by the angle calculation unit.

3. The control system for the continuum robot according to claim 2, wherein the angle calculation unit calculates, for each of the plurality of minute sections, the bending angle, the turning angle, and the torsional angle of the minute section, based on the bending angle and the turning angle of the bendable portion, the torsional angle acquired by the torsional angle acquisition unit, and a displacement from an initial position of the bendable portion.

4. The control system for the continuum robot according to claim 1, further comprising a control unit configured to control the drive unit to drive the wire, based on the length of the wire in the bendable portion obtained by the kinematics calculation unit.

5. The control system for the continuum robot according to claim 1,
wherein the continuum robot includes a plurality of the bendable portions arranged in series, the plurality of bendable portions including a first bendable portion and a second bendable portion provided at a position farther from the drive unit than the first bendable portion,
wherein the torsional angle acquisition unit acquires the torsional angle of the first bendable portion and the torsional angle of the second bendable portion,
wherein the kinematics calculation unit calculates a length of a first wire and a length of a second wire in the first bendable portion based on the torsional angle of the first bendable portion acquired by the torsional angle acquisition unit, and calculates a length of the second wire in the second bendable portion based on the torsional angle of the second bendable portion acquired by the torsional angle acquisition unit, the first wire being the wire for bending the first bendable portion, the second wire being the wire for bending the second bendable portion, and
wherein the control system for the continuum robot further comprises a second addition unit different from the addition unit, the second addition unit being configured to calculate a length of the second wire in the first bendable portion and the second bendable portion by adding the length of the second wire in the first bendable portion and the length of the second wire in the second bendable portion that are obtained by the kinematics calculation unit.

6. A control method for a continuum robot including a bendable portion configured to be bent by driving of a wire, and a drive unit configured to drive the wire, the control method comprising:

acquiring a torsional angle of the bendable portion; and performing a kinematics calculation to calculate a length of the wire in the bendable portion based on the acquired torsional angle, wherein the kinematics calculation includes:

performing a wire length calculation to calculate, for each of a plurality of minute sections obtained by dividing the bendable portion in a longitudinal direction thereof, a length of the wire in the minute section based on a bending angle, a turning angle, and a torsional angle of the minute section; and adding the lengths of the wire in the plurality of minute sections obtained in the wire length calculation to calculate the length of the wire in the bendable portion.

7. A non-transitory computer-readable storage medium storing a program for causing a computer to execute a control method for a continuum robot including a bendable portion configured to be bent by driving of a wire, and a drive unit configured to drive the wire, the control method comprising:

acquiring a torsional angle of the bendable portion; and performing a kinematics calculation to calculate a length of the wire in the bendable portion based on the acquired torsional angle, wherein the kinematics calculation includes:

performing a wire length calculation to calculate, for each of a plurality of minute sections obtained by dividing the bendable portion in a longitudinal direction thereof, a length of the wire in the minute section based on a bending angle, a turning angle, and a torsional angle of the minute section; and adding the lengths of the wire in the plurality of minute sections obtained in the wire length calculation to calculate the length of the wire in the bendable portion.

\* \* \* \* \*